United States Patent
Schaeffer et al.

(10) Patent No.: US 10,136,907 B2
(45) Date of Patent: Nov. 27, 2018

(54) METHODS OF LOCATING AND TREATING TISSUE IN A WALL DEFINING A BODILY PASSAGE

(71) Applicant: COOK MEDICAL TECHNOLOGIES LLC, Bloomington, IN (US)

(72) Inventors: Darin Schaeffer, Bloomington, IN (US); Daniel Dalenberg, Portage, MI (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 141 days.

(21) Appl. No.: 15/411,420

(22) Filed: Jan. 20, 2017

(65) Prior Publication Data

US 2017/0128092 A1    May 11, 2017

Related U.S. Application Data

(63) Continuation of application No. 14/449,207, filed on Aug. 1, 2014, now Pat. No. 9,549,748.

(Continued)

(51) Int. Cl.
*A61B 17/24* (2006.01)
*A61B 17/12* (2006.01)
(Continued)

(52) U.S. Cl.
CPC ........ *A61B 17/24* (2013.01); *A61B 17/12104* (2013.01); *A61B 17/12136* (2013.01);
(Continued)

(58) Field of Classification Search
CPC .............. A61B 17/24; A61B 17/12104; A61B 17/12136; A61B 2017/1205;
(Continued)

(56) References Cited

U.S. PATENT DOCUMENTS 2,649,092 A    8/1953   Wallace
3,521,620 A    7/1970   Cook
(Continued)

FOREIGN PATENT DOCUMENTS

CA    2403030    3/2003
EP    2368481    9/2011
(Continued)

OTHER PUBLICATIONS

Non-final Office Action dated Sep. 15, 2009 U.S. Appl. No. 11/800,292.
(Continued)

*Primary Examiner* — Katherine M Shi
(74) *Attorney, Agent, or Firm* — Buchanan Van Tuinen LLC

(57) ABSTRACT

Devices, kits, and methods of treatment are described. More particularly, methods of treating tissue of a passage wall defining a bodily passage, such as a sinus cavity, airway, or sinus passage are described. An exemplary method utilizes an elongate member having an elongate member proximal end, elongate member distal end, and an elongate member body that defines a curve.

20 Claims, 11 Drawing Sheets

Related U.S. Application Data

(60) Provisional application No. 61/861,029, filed on Aug. 1, 2013.

(51) Int. Cl.
 *A61M 25/00* (2006.01)
 *A61B 17/00* (2006.01)
 *A61M 25/10* (2013.01)

(52) U.S. Cl.
 CPC ... *A61M 25/0017* (2013.01); *A61B 2017/003* (2013.01); *A61B 2017/1205* (2013.01); *A61B 2017/246* (2013.01); *A61M 2025/1081* (2013.01); *A61M 2210/0681* (2013.01)

(58) Field of Classification Search
 CPC .......... A61B 1/00082; A61B 2017/003; A61B 17/12022; A61B 17/3421; A61M 2210/0681; A61M 2210/0618; A61M 25/0041; A61M 2025/1081; A61M 2029/025; A61M 25/10; A61M 25/1002
 USPC .......................................... 606/108, 196, 199
 See application file for complete search history.

(56) References Cited

U.S. PATENT DOCUMENTS

| | | |
|---|---|---|
| 3,625,200 A | 12/1971 | Muller |
| 4,790,812 A | 12/1988 | Hawkins et al. |
| 4,826,087 A | 5/1989 | Chinery |
| 4,886,067 A | 12/1989 | Palermo |
| 4,983,166 A | 1/1991 | Yamawaki |
| 5,125,395 A | 6/1992 | Adair |
| 5,308,318 A | 5/1994 | Plassche, Jr. |
| 5,441,483 A | 8/1995 | Avitall |
| 5,447,503 A | 9/1995 | Miller |
| 5,477,860 A | 12/1995 | Essen-Moller |
| 5,489,278 A | 2/1996 | Abrahamson |
| 5,509,900 A | 4/1996 | Kirkman |
| 5,534,007 A | 7/1996 | Germain et al. |
| 5,642,736 A | 7/1997 | Avitall |
| 5,643,171 A | 7/1997 | Bradshaw et al. |
| 5,658,301 A | 8/1997 | Lamaitre et al. |
| 5,674,197 A | 10/1997 | van Muiden et al. |
| 5,718,684 A | 2/1998 | Gupta |
| 5,769,821 A | 6/1998 | Abrahamson et al. |
| 5,807,398 A | 9/1998 | Shaknovich |
| 5,865,800 A | 2/1999 | Mirarchi et al. |
| 5,916,214 A | 6/1999 | Cosio et al. |
| 5,938,582 A | 8/1999 | Ciamacco et al. |
| 5,954,050 A | 9/1999 | Christopher |
| 6,033,378 A | 3/2000 | Lundquist et al. |
| 6,071,263 A | 6/2000 | Kirkman |
| 6,117,386 A | 9/2000 | Stiger |
| 6,126,649 A | 10/2000 | VanTassel et al. |
| 6,159,158 A | 12/2000 | Lowe |
| 6,217,554 B1 | 4/2001 | Green |
| 6,338,735 B1 | 1/2002 | Stevens |
| 6,383,206 B1 | 5/2002 | Gillick et al. |
| 6,447,530 B1 | 9/2002 | Ostrovsky et al. |
| 6,450,988 B1 | 9/2002 | Bradshaw |
| 6,485,500 B1 | 11/2002 | Kokish et al. |
| 6,491,662 B1 | 12/2002 | Liprie et al. |
| 6,500,167 B1 | 12/2002 | Webster, Jr. |
| 6,500,182 B2 | 12/2002 | Foster |
| 6,508,833 B2 | 1/2003 | Pavcnik et al. |
| 6,527,737 B2 | 3/2003 | Kaneshige |
| 6,533,783 B1 | 3/2003 | Tollner |
| 6,558,349 B1 | 5/2003 | Kirkman |
| 6,572,610 B2 | 6/2003 | Kovalcheck et al. |
| 6,629,987 B1 | 10/2003 | Gambale |
| 6,679,860 B2 | 1/2004 | Stiger |
| 6,692,484 B1 | 2/2004 | Karpiel et al. |
| 6,695,858 B2 | 2/2004 | Dubrul et al. |
| 6,755,812 B2 | 6/2004 | Peterson et al. |
| 6,918,929 B2 | 7/2005 | Udipi et al. |
| 6,932,829 B2 | 8/2005 | Majercak |
| 7,037,290 B2 | 5/2006 | Gardeski et al. |
| 7,144,408 B2 | 12/2006 | Keegan et al. |
| 7,232,462 B2 | 6/2007 | Schaeffer |
| 7,261,850 B2 | 8/2007 | van Ockenburg et al. |
| 7,269,453 B2 | 9/2007 | Mogul |
| 7,503,914 B2 | 3/2009 | Coleman et al. |
| 7,520,876 B2 | 4/2009 | Ressemann et al. |
| 7,658,305 B2 | 2/2010 | Voegele et al. |
| 7,678,099 B2 | 3/2010 | Ressemann et al. |
| 7,785,252 B2 | 8/2010 | Danitz et al. |
| 7,785,315 B1 | 8/2010 | Muni et al. |
| 7,803,130 B2 | 9/2010 | Ryan et al. |
| 7,811,277 B2 | 10/2010 | Boulais |
| 7,846,148 B2 | 12/2010 | Zhou |
| 7,867,218 B1 | 1/2011 | Voda |
| 7,892,233 B2 | 2/2011 | Hall et al. |
| 7,909,862 B2 | 3/2011 | Garrison |
| 7,930,016 B1 | 4/2011 | Saadat |
| 7,935,108 B2 | 5/2011 | Baxter et al. |
| 7,959,601 B2 | 6/2011 | McDaniel et al. |
| 8,029,461 B2 | 10/2011 | Thielen et al. |
| 8,048,101 B2 | 11/2011 | Lee-Sepsick et al. |
| 8,066,664 B2 | 11/2011 | LaDuca et al. |
| 8,070,693 B2 | 12/2011 | Ayala et al. |
| 8,080,000 B2 | 12/2011 | Makower et al. |
| 8,083,879 B2 | 12/2011 | Swinehart et al. |
| 8,090,433 B2 | 1/2012 | Makower et al. |
| 8,114,113 B2 | 2/2012 | Becker |
| 8,118,803 B1 | 2/2012 | Chow |
| 8,142,422 B2 | 3/2012 | Makower et al. |
| 8,182,467 B2 | 5/2012 | Nguyen et al. |
| 8,197,453 B2 | 6/2012 | Zhou |
| 8,216,210 B2 | 7/2012 | Ostrovsky et al. |
| 8,277,478 B2 | 10/2012 | Drontle et al. |
| 8,282,667 B2 | 10/2012 | Drontle et al. |
| 8,369,923 B2 | 2/2013 | de la Rama et al. |
| 8,403,977 B2 | 3/2013 | Case |
| 8,424,534 B2 | 4/2013 | Lyons et al. |
| 8,425,466 B2 | 4/2013 | Sargent, Jr. |
| 8,430,864 B2 | 4/2013 | Schultz |
| 8,535,310 B2 | 9/2013 | Hardin, Jr. et al. |
| 8,535,349 B2 | 9/2013 | Chen et al. |
| 8,603,185 B2 | 12/2013 | Shah et al. |
| 8,740,843 B2 | 6/2014 | Eaton et al. |
| 8,758,231 B2 | 6/2014 | Bunch et al. |
| 8,899,225 B2 | 12/2014 | Bosel |
| 8,911,399 B2 | 12/2014 | Boatman |
| 9,549,748 B2 | 1/2017 | Schaeffer et al. |
| 2001/0039450 A1 | 11/2001 | Pavcnik et al. |
| 2002/0115983 A1 | 8/2002 | Sekino et al. |
| 2003/0004460 A1 | 1/2003 | Bedell |
| 2003/0032977 A1 | 2/2003 | Brady |
| 2003/0050694 A1 | 3/2003 | Heneveld et al. |
| 2004/0087965 A1 | 5/2004 | Hebert et al. |
| 2004/0087996 A1 | 5/2004 | Forcucci et al. |
| 2004/0225322 A1 | 11/2004 | Garrison et al. |
| 2005/0171592 A1 | 8/2005 | Majercak |
| 2005/0256452 A1 | 11/2005 | DeMarchi et al. |
| 2006/0063973 A1 | 3/2006 | Makower et al. |
| 2006/0079787 A1 | 4/2006 | Whiting et al. |
| 2007/0093781 A1 | 4/2007 | Kugler et al. |
| 2007/0167682 A1 | 7/2007 | Goldfarb et al. |
| 2007/0219464 A1 | 9/2007 | Davis et al. |
| 2007/0250105 A1 | 10/2007 | Ressemann et al. |
| 2007/0293727 A1 | 12/2007 | Goldfarb et al. |
| 2008/0097154 A1 | 4/2008 | Makower et al. |
| 2008/0172033 A1* | 7/2008 | Keith ................. A61B 1/00154 604/506 |
| 2008/0243067 A1 | 10/2008 | Rottenberg et al. |
| 2008/0249483 A1 | 10/2008 | Slenker et al. |
| 2008/0281156 A1 | 11/2008 | Makower et al. |
| 2008/0287918 A1 | 11/2008 | Rosenman et al. |
| 2009/0030274 A1 | 1/2009 | Goldfarb et al. |
| 2009/0043299 A1 | 2/2009 | Racz |
| 2009/0093823 A1 | 4/2009 | Chang et al. |
| 2009/0198153 A1 | 8/2009 | Shriver |
| 2009/0326450 A1 | 12/2009 | Ostrovsky et al. |

(56) References Cited

U.S. PATENT DOCUMENTS

| | | | |
|---|---|---|---|
| 2010/0010309 A1 | 1/2010 | Kitagawa |
| 2010/0030113 A1 | 2/2010 | Morriss et al. |
| 2010/0076269 A1 | 3/2010 | Makower et al. |
| 2010/0099946 A1 | 4/2010 | Jenkins et al. |
| 2010/0211007 A1 | 8/2010 | Lesch, Jr. et al. |
| 2010/0217261 A1 | 8/2010 | Watson |
| 2010/0262075 A1 | 10/2010 | Danitz et al. |
| 2010/0280316 A1 | 11/2010 | Dietz et al. |
| 2010/0312101 A1 | 12/2010 | Drontle et al. |
| 2010/0331776 A1 | 12/2010 | Salahieh et al. |
| 2011/0009700 A1 | 1/2011 | Ostrovsky et al. |
| 2011/0015734 A1 | 1/2011 | Gonzales et al. |
| 2011/0022172 A1 | 1/2011 | Gonzales et al. |
| 2011/0112476 A1 | 5/2011 | Kauphusman et al. |
| 2011/0190831 A1 | 8/2011 | Mafi et al. |
| 2011/0218492 A1 | 9/2011 | McDaniel et al. |
| 2011/0224652 A1 | 9/2011 | Drontle et al. |
| 2011/0264134 A1 | 10/2011 | Drontle et al. |
| 2011/0313392 A1 | 12/2011 | Varghese et al. |
| 2012/0010646 A1 | 1/2012 | Keith et al. |
| 2012/0016341 A1 | 1/2012 | Chambers |
| 2012/0046664 A1 | 2/2012 | McGuckin, Jr. et al. |
| 2012/0071727 A1 | 3/2012 | Hanson et al. |
| 2012/0095448 A1 | 4/2012 | Kajii |
| 2012/0101441 A1 | 4/2012 | Sargent, Jr. |
| 2012/0116254 A1 | 5/2012 | Morriss |
| 2012/0136207 A1 | 5/2012 | Goldfarb et al. |
| 2012/0162401 A1 | 6/2012 | Melder et al. |
| 2012/0197240 A1 | 8/2012 | Smith et al. |
| 2012/0238952 A1 | 9/2012 | Mitchell et al. |
| 2012/0265055 A1 | 10/2012 | Melsheimer et al. |
| 2013/0041314 A1 | 2/2013 | Dillon |
| 2013/0046138 A1 | 2/2013 | McLawhorn |
| 2013/0226146 A1 | 8/2013 | Tekulve |
| 2013/0238003 A1 | 9/2013 | Fischer et al. |
| 2014/0088355 A1 | 3/2014 | Schaeffer |
| 2015/0039014 A1 | 2/2015 | Schaeffer et al. |

FOREIGN PATENT DOCUMENTS

| | | |
|---|---|---|
| GB | 2465621 | 6/2010 |
| WO | 98043530 | 10/1998 |
| WO | 2001026726 | 4/2001 |
| WO | 2003001986 | 1/2003 |

OTHER PUBLICATIONS

EyeMAX CCD Laparscopes [online brochure]. Richard Wolf GmbH [retrieved Nov. 15, 2013]. Retrieved from the Internet: URL: http://www.richard-wolf.com/uploads/media/A_658_Eyemax_GB_l07.pdf. pp. 1-8.

EyeMAX Flexible LED Cystoscope [online brochure]. Richard Wolf GmbH [retrieved Nov. 15, 2013]. Retrieved from the internet: URL: http://www.richardwolfusa.com/fileadmin/images/content/USA_data/PDF_documents/Urology/Flexible_LED_Digital_Cystoscope_brochure_01312013.pdf. pp. 1-4.

Olympus Naso-laryngoscopes. Olympus. Retrieved from the internet: URL: www.olympuskeymed.com, pp. 1-3.

XprESS Multi-Sinus Dilation Tool Using Bending Tool. Instructions for Use, Entellus Medical, Sep. 2011, pp. 1-7.

XprESS Multi-Sinus Dilation Tool. Instructions for Use, Entellus Medical, May 2011, pp. 1-7.

A trial study of RhinoSleep for the diagnosis of sleep apnea. Psychiatry and Clinical Neurosciences. Jun. 2001, pp. 1-2.

E.G. Scan—Trans-nasal, disposable system for upper GI screening [online brochure]. SynMed Ltd. [retrieved Jun. 4, 2014]. Retrieved from the internet: URL: http://www.synmed.co.uk/products/eg_scan/pdf/SynMed_E.G.Scan_Brochure.pdf.

Drug-induced Sleep Endoscopy webpage [online], Eric J. Kezirian [retrieved Nov. 14, 2013]. Retrieved from the internet: URL: http://www.sleep-doctor.com/surgical-treatment-overview/drug-induced-sleep-endoscopy/.

EyeMax webpage [online], Richard Wolf [retrieved Nov. 14, 2013]. Retrieved from the Internet: URL: http://www.richard-wolf.com/en/human-medicine/visualisation/video-endoscopes/ccd-endoscopes.html.

International Searching Authority. International Search Report and Written Opinion, for International App. No. PCT/US2014/018878. dated Jun. 11, 2014. p. 1-12.

European Patent Office, Extended European Search Report, App. No. 1318580.2, dated Jan. 7, 2014, pp. 1-5.

Cook Medical. Reuter Tip Deflecting Wire Guide Handle and Wire Guides [pdf]. Feb. 2012. pp. 1-32. Retrieved from <https://www.cookmedical.com/data/IFU_PDF/T_TDWIRE_REV0.PDF>.

Atos Medical. SinoJect [pdf]. pp. 1-2. Retrieved from <http://www.atosmedical.com/For_professionals/Focus_areas/~/media/Sweden/MC0766-NoEN.pdf>.

Acclarent. Relieva Spin: Balloon Sinuplasty System [pdf]. 2012. pp. 1-3. Retrieved from <http://www.acclarent.com/sites/default/files/product/pdf/Relieva%20Spin%20Brochure%20MKT02189%20Rev%20C%20final.pdf>.

Acclarent. Balloon Sinuplasty System [website]. 2014. pp. 1-3. Retrieved from <http://www.acclarent.com/solutions/products/balloon-sinuplasty-system>.

Acclarent. Balloon Sinuplasty System [website]. 2012. pp. 1-2. Retrieved from <http://www.acclarent.com/solutions/products/balloon-sinuplasty-system/>.

* cited by examiner

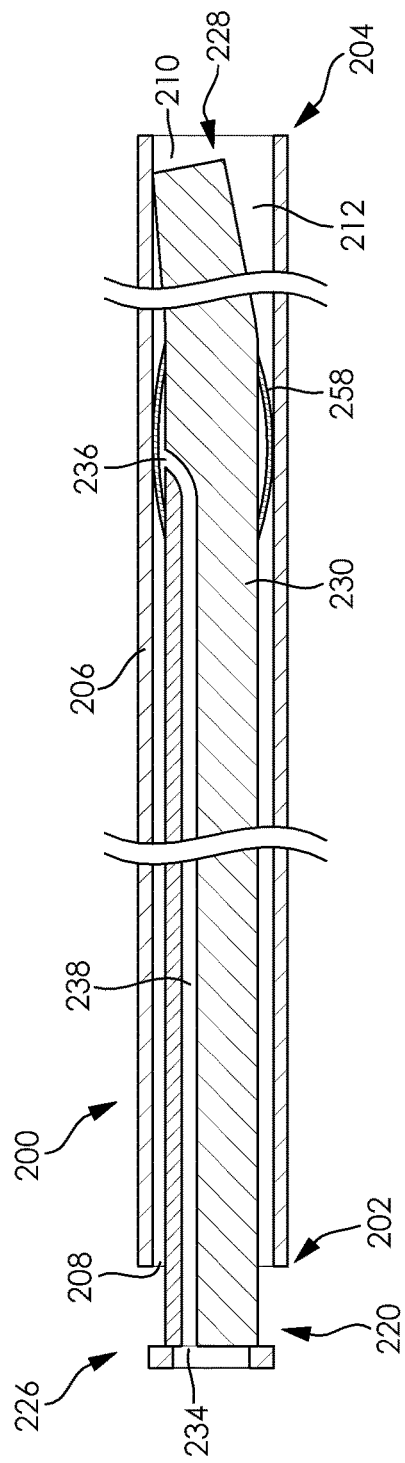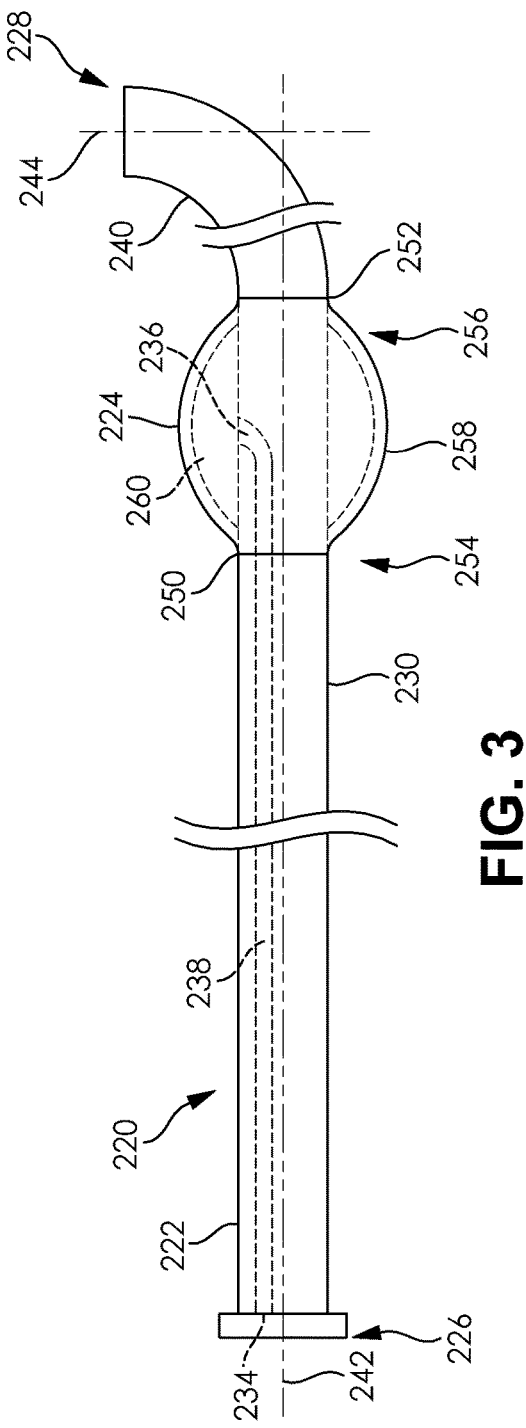

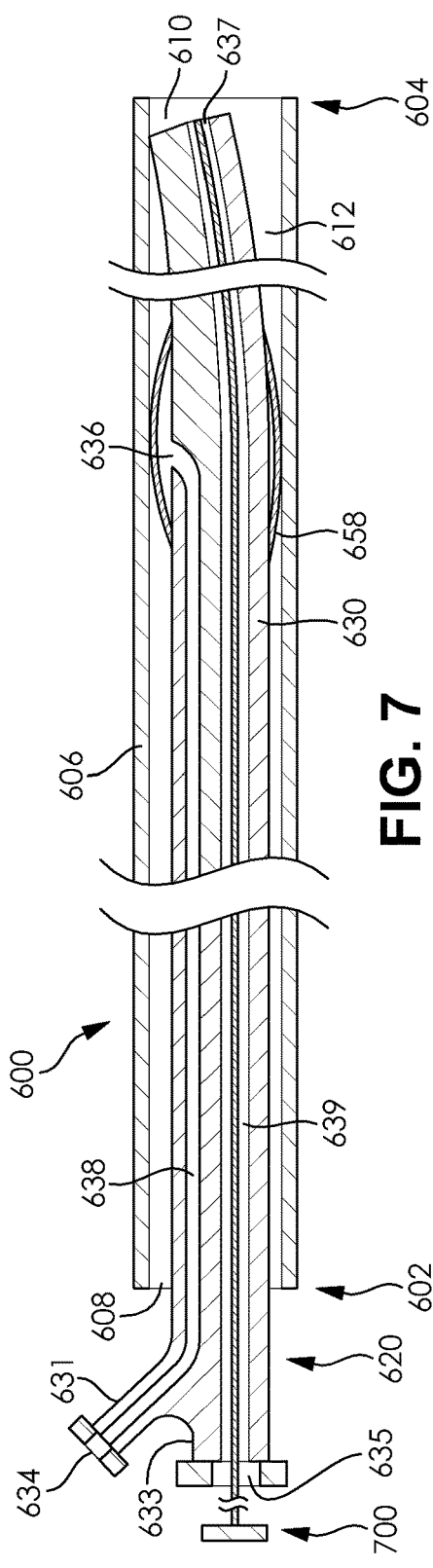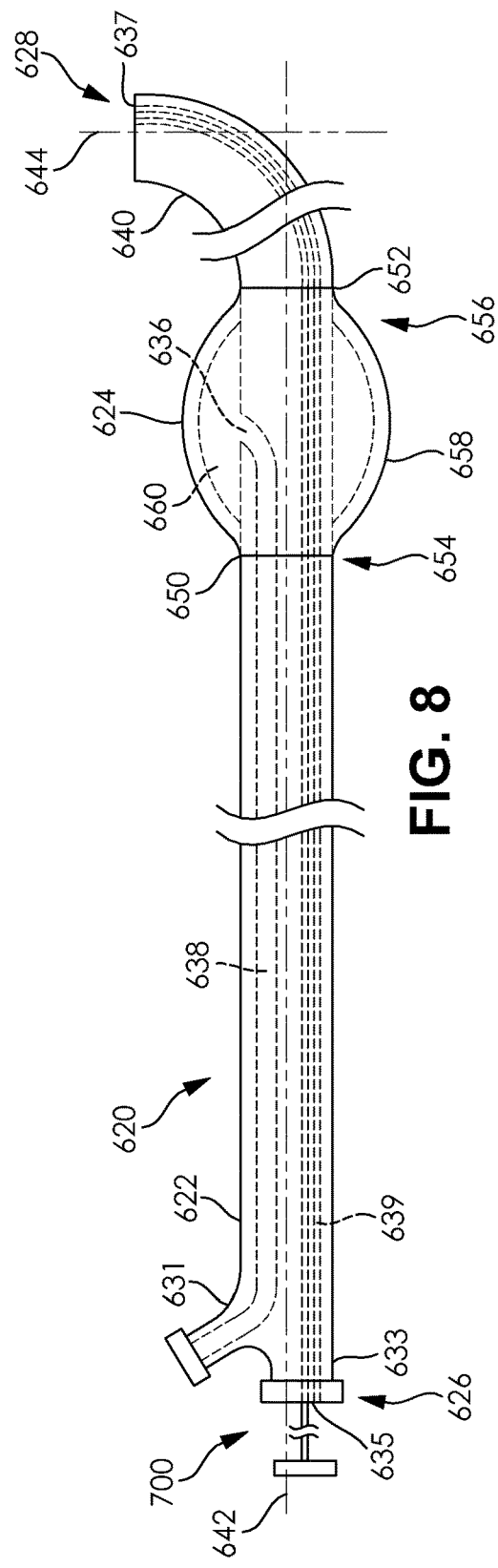

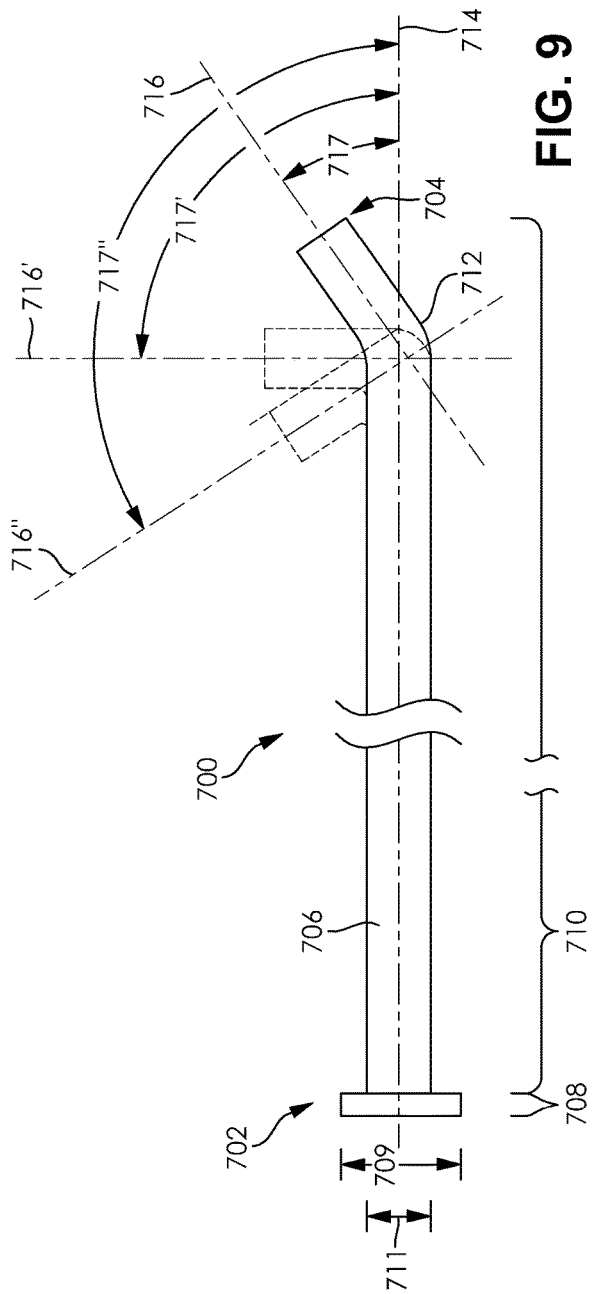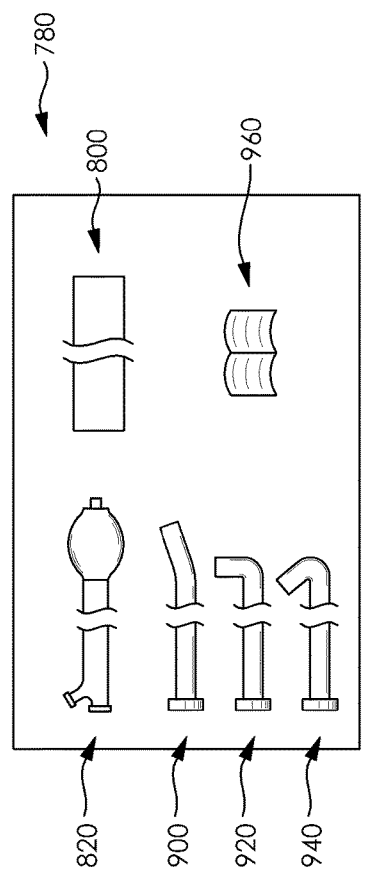
FIG. 9
FIG. 10

METHODS OF LOCATING AND TREATING TISSUE IN A WALL DEFINING A BODILY PASSAGE

RELATED APPLICATION

This application is a continuation of U.S. patent application Ser. No. 14/449,207, which was filed on Aug. 1, 2014 and which claims the benefit of U.S. Provisional Application No. 61/861,029, filed on Aug. 1, 2013. The disclosure of each of these related applications is hereby incorporated into this disclosure in its entirety.

FIELD

The disclosure relates generally to methods of treatment. More particularly, the disclosure relates to methods of locating and treating tissue in a wall defining a bodily passage, such as a sinus passage, airway, or sinus cavity. The disclosure also relates to devices and kits for treating tissue in a wall defining a bodily passage, such as a sinus passage, airway, or sinus cavity.

BACKGROUND

To treat stenosis—the narrowing of a bodily passage—physicians frequently dilate the bodily passage using a balloon catheter. For example, when functioning normally, sinus passages allow mucus to drain from the sinus cavities and allow air to circulate throughout the respiratory system. However, when a sinus passage, such as an ostium, becomes blocked and prevents the outflow of material from a sinus cavity, infection can occur resulting in sinusitis.

To treat these conditions, physicians sometimes systematically administer drugs at a treatment site within the sinus or prescribe antibiotics to reduce inflammation and/or treat the infection. Alternatively, balloon sinuplasty—the dilation of a sinus passage using a balloon catheter—can be performed to unblock the sinus passage. Conventional sinuplasty procedures advance a balloon catheter over a previously placed guide wire and move the balloon to an inflated configuration to effectuate dilation and unblock the obstructed passage. However, these procedures are complicated by the need to navigate and position the guide wire prior to positioning the balloon catheter at a point of treatment (e.g., within an ostium). For example, the guide wire must be advanced through the nasal passage and then navigated through the ostium, which may be disposed at an abrupt angle to the nasal passage. The structural arrangement of the nasal passage relative to the ostium increases the difficulty and time required to advance the guide wire through the ostium such that a balloon catheter can be advanced to the point of treatment.

Therefore, a need exists for improved devices, methods, and kits for locating and treating tissue in a wall defining a bodily passage, such as a sinus passage, airway, or sinus cavity.

SUMMARY

Several exemplary devices, methods, and kits for locating and treating tissue in a wall defining a bodily passage, such as a sinus passageway, airway, or sinus cavity are described herein.

Additional understanding of the exemplary devices, methods, and kits can be obtained by review of the detailed description, presented below, and the referenced drawings.

BRIEF DESCRIPTION OF THE DRAWINGS

FIG. 2 is a sectional view of an exemplary catheter disposed within a cannula. The catheter is in the first straight, or substantially straight, configuration.

FIG. 3 is a side view of the exemplary catheter illustrated in FIG. 2, free of the cannula and in the second curved configuration.

FIG. 7 is a sectional view of an exemplary insert disposed within another exemplary catheter. The catheter is disposed within a cannula and is in the first straight, or substantially straight, configuration.

FIG. 8 is a side view of the exemplary insert and catheter illustrated in FIG. 7, free of the cannula and in the second curved configuration.

FIG. 9 is a side view of the exemplary insert illustrated in FIGS. 7 and 8, free of the catheter and in the second curved configuration.

FIG. 10 illustrates an exemplary kit.

DETAILED DESCRIPTION

Figure 1:
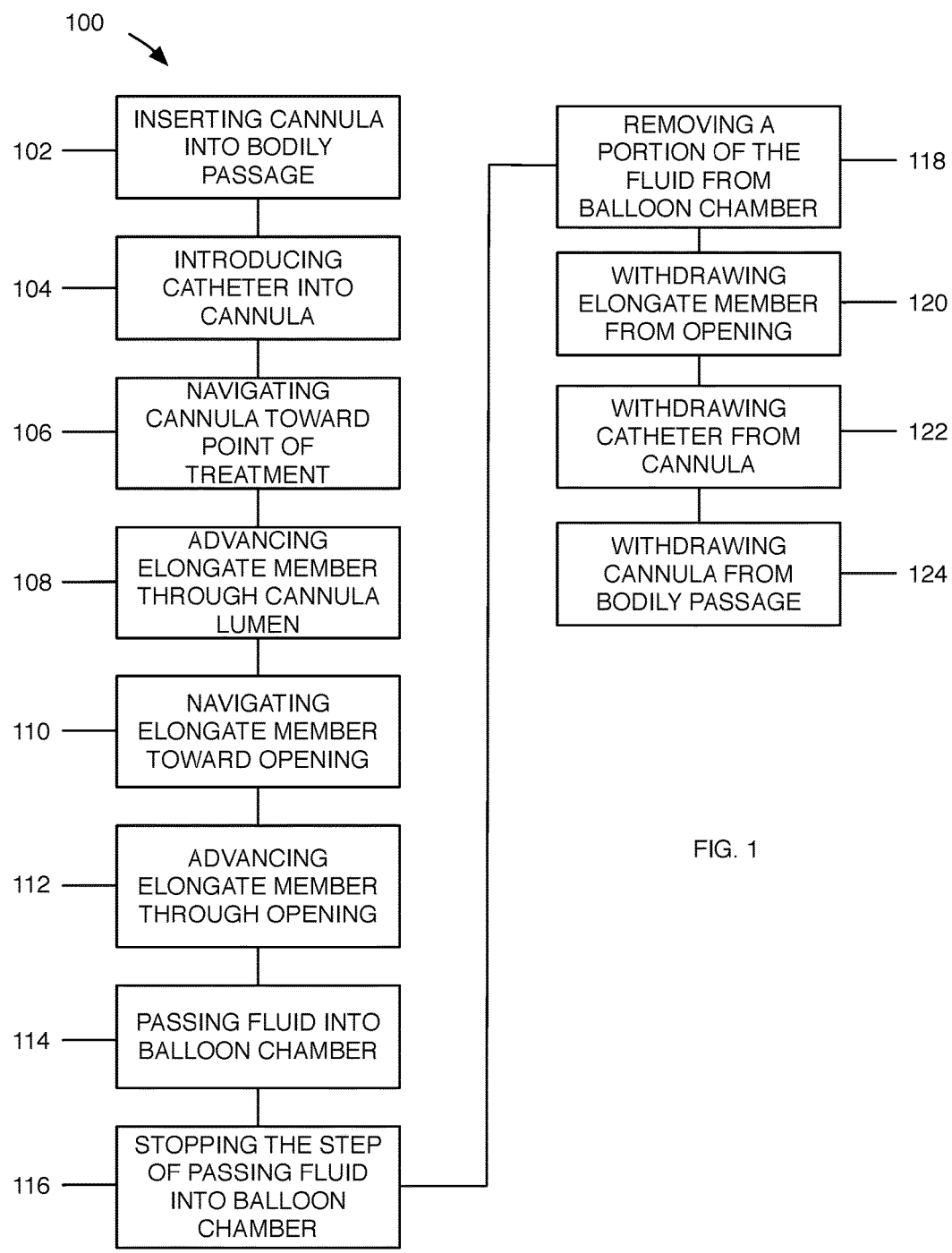
FIG. 1 is a flowchart representation of an exemplary method of treating tissue in a wall defining a bodily passage.

The following detailed description and the appended drawings describe and illustrate various exemplary methods, delivery devices, cannulas, and catheters. The description and drawings are exemplary in nature and are provided to enable one skilled in the art to practice one or more exemplary methods and/or make one or more exemplary delivery devices, cannulas, and/or catheters. They are not intended to limit the scope of the claims in any manner.

The use of "e.g.," "etc.," "for instance," "in example," and "or" and grammatically related terms indicate non-exclusive alternatives without limitation, unless otherwise noted. The use of "optionally" and grammatically related terms means that the subsequently described element, event, feature, or circumstance may or may not be present or occur, and that the description includes instances where said element, event, feature, or circumstance occurs and instances where it does not. The use of "exemplary" refers to "an example of" and is not intended to convey a meaning of an ideal or preferred embodiment. The use of "attached" refers to the fixed, releasable, or integrated association of two or more elements and/or devices. Thus, the term "attached" includes releasably attaching or fixedly attaching two or more elements and/or devices. As used herein, the terms "proximal" and "distal" are used to describe opposing axial ends of the particular element or feature being described. The term "bodily passage" or "body passage" refers to any passage within the body of an animal, including, but not limited to, humans, and includes elongate passages. The term "sinus passage" refers to the nasal passages and includes, but is not limited to, eustachian tube(s), primary ostium, accessory ostium, and/or an opening defined by a ventilation tube. The term "airway" refers to any airway including, but not limited to, the nasopharynx, oropharynx, pharynx, trachea, bronchial tubes, and/or lungs. The term "sinus cavity" refers to the frontal, ethmoid, sphenoid, and/or maxillary sinus.

Various methods of treatment are provided. These methods include treating tissue in a wall defining a bodily passage, such as a sinus passage, airway, or sinus cavity. While some methods of treating tissue in a wall defining a bodily passage are exemplified by methods of treating an opening defined by the wall of a bodily passage or treating tissue in a wall defining a sinus passage, airway, or sinus cavity, the methods can also be used to treat tissue in a wall defining any other suitable bodily passage, and skilled artisans will be able to select a suitable tissue for treatment with a particular method based on various considerations, such as the nature of the treatment to be performed. Examples of other tissues considered suitable to treat using one or more of the methods and/or steps described herein include, but are not limited to, the tissue in a wall defining the urinary tract, and the tissue in a wall defining any other bodily passage considered suitable for a particular application.

While the methods described herein are shown and described as a series of acts, it is to be understood and appreciated that the methods are not limited by the order of acts, as some acts may, in accordance with these methods, be omitted, occur in different orders with other acts described herein, and/or concurrently with other acts described herein.

FIG. 1 is a flowchart representation of an exemplary method 100 of treating tissue in a passage wall defining a bodily passage.

A step 102 comprises inserting a cannula having a cannula proximal end, a cannula distal end, and a cannula body defining a cannula lumen into a bodily passage such that the cannula distal end is disposed within the bodily passage. Another step 104 comprises introducing a catheter having an elongate member and balloon into the cannula lumen. The elongate member having an elongate member proximal end, elongate member distal end, elongate member length, and an elongate member body that defines an inflation lumen and an elongate member curve. The elongate member length extends from the elongate member proximal end to the elongate member distal end. The elongate member curve is defined along a portion of the elongate member. The elongate member is adapted to move between a first straight, or substantially straight, configuration in which the portion of the elongate member that defines the elongate member curve is straight, or substantially straight, when disposed within the cannula lumen and a second curved configuration in which the portion of elongate member that defines the elongate member curve is curved when free of, or disposed outside of, the cannula lumen. The balloon is disposed on the elongate member and has a balloon wall that defines a balloon chamber in communication with the inflation lumen. The balloon is moveable between a first deflated configuration and a second inflated configuration as fluid is moved into and out of the balloon chamber. Another step 106 comprises navigating the cannula toward a point of treatment within the bodily passage. The point of treatment comprises an opening defined by the wall of the bodily passage. Another step 108 comprises advancing the elongate member distally through the cannula lumen such that the portion of the elongate member that defines the elongate member curve is free of, or disposed outside of, the cannula lumen and the elongate member moves from the first configuration to the second configuration. Thus, the elongate member adopts a curved configuration. Another step 110 comprises navigating the elongate member distal end toward the opening defined by the passage wall. Another step 112 comprises advancing the elongate member distal end through the opening defined by the passage wall such that the balloon is positioned through the opening. Another step 114 comprises passing a fluid through the inflation lumen and into the balloon chamber to move the balloon toward the second inflated configuration. Another step 116 comprises stopping the step of passing a fluid through the inflation lumen and into the balloon chamber. Another step 118 comprises removing a portion of the fluid from the balloon chamber. Another step 120 comprises withdrawing the elongate member from the opening defined by the passage wall. Another step 122 comprises withdrawing the catheter from the cannula lumen. Another step 124 comprises withdrawing the cannula from the bodily passage.

Step 102 can be accomplished by applying a distally-directed force (e.g., toward bodily passage) on any suitable portion of a cannula such that the cannula distal end is passed into the bodily passage (e.g., through an opening defined by a passage wall). Any suitable cannula having any suitable structural arrangement can be used to accomplish step 102, and skilled artisans will be able to select a suitable cannula and structural arrangement for a cannula according to a particular embodiment based on various considerations, including the tissue desired to be treated. FIG. 2 illustrates an exemplary cannula 200 having a cannula proximal end 202, a cannula distal end 204, and a cannula body 206. The cannula body 206 defines a cannula first opening 208, a cannula second opening 210, and a cannula lumen 212 that extends from the cannula first opening 208 to the cannula second opening 210.

The cannula 200 can be formed of any suitable material and fabricated using any suitable technique, and skilled artisans will be able to select a suitable material to form a cannula and a suitable technique to fabricate a cannula according to a particular embodiment based on various considerations, including the desired flexibility of the cannula. Example materials considered suitable to form a cannula include, but are not limited to, biocompatible materials, materials that can be made biocompatible, metals such as stainless steel, titanium, nitinol, cobalt chromium, polymers, Pebax (Pebax is a registered trademark of Ato Chimie Corporation of Allee des Vosges, Courbevoie, France), nylon, polyethylene, polyurethane, silicone, coiled materials, braided materials, and any other material considered suitable for a particular application.

Step 104 can be accomplished by applying a distally-directed force (e.g., toward bodily passage) on any suitable portion of a catheter such that a portion of the catheter (e.g., portion of elongate member), or at least a portion of the catheter (e.g., at least a portion of elongate member), is passed into the cannula lumen (e.g., through an opening defined by the cannula body, cannula first opening 208). Any suitable catheter having any suitable structural arrangement can be used to accomplish step 104, and skilled artisans will be able to select a suitable catheter and structural arrangement for a catheter according to a particular embodiment based on various considerations, including the procedure intended to be performed. FIGS. 2 and 3 illustrate an exemplary balloon catheter 220 comprising an elongate member 222 and balloon 224.

Optionally, a catheter can be preloaded within a cannula such that step 104 can be omitted from method 100. Alternatively, step 104 can be accomplished prior to step 102 such that a catheter is introduced into a cannula prior to the cannula being introduced into a bodily passage.

The elongate member 222 can be formed of any suitable material and fabricated using any suitable technique, and skilled artisans will be able to select a suitable material to form an elongate member and a suitable technique to fabricate an elongate member according to a particular embodiment based on various considerations, including the desired flexibility of the elongate member. Example materials considered suitable to form an elongate member include, but are not limited to, biocompatible materials, materials that can be made biocompatible, metals such as stainless steel, titanium, nitinol, cobalt chromium, polymers, Pebax (Pebax is a registered trademark of Ato Chimie Corporation of Allee des Vosges, Courbevoie, France), nylon, polyethylene, polyurethane, silicone, coiled materials, braided materials, and any other material considered suitable for a particular application.

The elongate member 222 can have any suitable outside diameter and length, and skilled artisans will be able to select a suitable outside diameter and length for an elongate member according to a particular embodiment based on various considerations, including the desired bodily passage within which the catheter is intended to be used. It is considered advantageous for the elongate member 222 to have an outside diameter that is less than the inside diameter of the cannula lumen 212. It is also considered advantageous for the elongate member 222 to have an elongate member length that is greater than the length of cannula 200.

In the illustrated embodiment, the elongate member 222 comprises an elongate member proximal end 226, an elongate member distal end 228, and an elongate member body 230. The elongate member 222 has an elongate member length that extends from the elongate member proximal end 226 to the elongate member distal end 228. The elongate member body 230 defines an elongate member first opening 234, an elongate member second opening 236, an inflation lumen 238, and an elongate member curve 240 (e.g., predefined curve).

In the illustrated embodiment, the elongate member first opening 234 is disposed on the elongate member proximal end 226 and the elongate member second opening 236 is disposed between the elongate member proximal end 226 and the elongate member distal end 228. The inflation lumen 238 extends from the elongate member first opening 234 to the elongate member second opening 236. The elongate member body 230 defines the elongate member curve 240 between the elongate member proximal end 226 and the elongate member distal end 228. In the illustrated embodiment, the elongate member curve 240 is defined between the balloon 224 and the elongate member distal end 228.

In the illustrated embodiment, the elongate member 222 is adapted to move between a first straight, or substantially straight, configuration and a second curved configuration. In the first straight, or substantially straight, configuration, the portion of the elongate member 222 that defines the elongate member curve 240 is straight, or substantially straight, when it is disposed within the cannula lumen 212, as illustrated in FIG. 2. For example, in embodiments in which the elongate member 222, a portion of the elongate member, or an element disposed within the elongate member 222 is biased to a curved configuration, and the elongate member 222 is disposed within the cannula lumen 212, the elongate member 222 forms to the structural arrangement of the cannula lumen 212 such that a portion of the elongate member 222 (e.g., elongate member distal end 228) contacts the inner wall of the cannula 200 (e.g., the elongate member 222 forms a slight curve within the cannula lumen 212). In the second curved configuration, the portion of the elongate member 222 that defines the elongate member curve 240 is curved when it is free of, or disposed outside of, the cannula lumen 212, as illustrated in FIG. 3. Thus, the elongate member 222 is biased to the second curved configuration. The portion of the elongate member 222 that forms a curve has a first radius of curvature when it is disposed within the cannula lumen 212 and a second radius of curvature when it is free of the cannula lumen 212 that is less than the first radius of curvature.

The elongate member 222 has an elongate member first axis 242 and an elongate member second axis 244 disposed at an angle to the elongate member first axis 242. The elongate member first axis 242 extends through a portion, or the entirety, of the elongate member body 230 that is disposed proximal to the elongate member curve 240. The elongate member second axis 244 extends through the elongate member first axis 242 and through the elongate member distal end 228 (e.g., center of elongate member distal end 228) when the elongate member 222 is in the second curved configuration.

The elongate member 222 can define any suitable angle between the elongate member first axis 242 and the elongate member second axis 244, and skilled artisans will be able to select a suitable angle to define between an elongate member first axis and an elongate member second axis according to a particular embodiment based on various considerations, including the procedure intended to be performed. Example angles considered suitable to define between an elongate member first axis and an elongate member second axis include, but are not limited to, acute angles, obtuse angles, a 45 degree angle, a substantially 45 degree angle, an angle about 45 degrees, a 90 degree angle, a substantially 90 degree angle, an angle about 90 degrees, a 135 degree angle, a substantially 135 degree angle, an angle about 135 degrees, and any other angle considered suitable for a particular application. For example, the inventors have determined that when used within the sinus (e.g., sinus passage, airway, sinus cavity), a 90 degree angle, substantially 90 degree angle, or angle about 90 degrees, is considered advantageous.

The elongate member curve 240 can be formed in the elongate member 222 using any suitable technique, and skilled artisans will be able to select a suitable technique to form a curve in an elongate member according to a particular embodiment based on various considerations, including the material that forms an elongate member. An example technique considered suitable to form a curve in an elongate member includes, but is not limited to, positioning the elongate member in the second curved configuration and then applying heat to the portion of the elongate member in which it is desired to form a curve such that the curve is incorporated into the material that forms the elongate member.

While the elongate member curve 240 has been illustrated as defined between the balloon 224 and the elongate member distal end 228, a curve can be defined along any suitable portion, or the entirety, of an elongate member. Skilled artisans will be able to select a suitable portion of an elongate member to define a curve according to a particular embodiment based on various considerations, including the procedure intended to be performed. Example portions of an elongate member considered suitable to define a curve, include, but are not limited to, defining a curve from an elongate member proximal end to an elongate member distal end, between an elongate member proximal end and an elongate member distal end, between an elongate member proximal end and a balloon proximal end, between an elongate member proximal end and a balloon distal end, between a balloon proximal end and a balloon distal end, between a balloon distal end and an elongate member distal end, and any other portion of an elongate member considered suitable for a particular application.

While the elongate member curve 240 has been illustrated as formed in the elongate member 222, a curve can alternatively be defined by the body of a separate elongate member, or length of material, and attached to the elongate member, elongate member distal end, embedded along the entire length, or a portion of the length, of the elongate member, or disposed within a lumen defined by an elongate member. For example, a separate elongate member having an elongate member proximal end, elongate member distal end, and elongate member body can define a curve, such as described above with respect to elongate member 222. The separate elongate member can then be attached to, or embedded within, the elongate member of a catheter using any suitable method of attachment. Skilled artisans will be able to select a suitable method of attachment between the elongate member of a catheter and a separate elongate member that defines a curve according to a particular embodiment based on various considerations, including the material that forms the elongate member of the catheter. Example methods of attachment considered suitable include, but are not limited to, heat fusing, using adhesives, mechanical connections, welding, and any other method of attachment considered suitable for a particular application. In these embodiments, the material that forms the elongate member and the separate elongate member that defines a curve can be the same, or different from one another. Thus, the elongate member of a catheter can comprise a first material and the separate elongate member can comprise a second material that is the same as the first material, or different from the first material. Example materials considered suitable to form the elongate member of a catheter and a separate elongate member that defines a curve include, but are not limited to, nitinol, those described herein (e.g., with respect to elongate member 222), and any other material considered suitable for a particular embodiment.

The elongate member proximal end 226 can include any suitable connector and/or adapter capable of attaching, or assisting with attaching, one or more devices to the elongate member 222. Skilled artisans will be able to select a suitable connector and/or adapter to include on an elongate member according to a particular embodiment based on various considerations, including the materials that form the elongate member. Example connectors and/or adapters considered suitable to include on an elongate member include, but are not limited to, threaded connectors, Tuohy Borst adapters, luer lock connectors, and any other connector and/or adapter considered suitable for a particular application.

Optionally, the elongate member 222 can comprise a seeking device disposed on the elongate member distal end 228, near the elongate member distal end 228, or adjacent the elongate member distal end 228. The seeking device can be formed of any suitable material and can comprise any suitable structure that can be used to locate an opening formed by the wall of a bodily passage. The seeking device can be a separate component attached to the elongate member distal end 228, or be formed as part of the elongate member 222. Example materials considered suitable to form a seeking device include, but are not limited to, biocompatible materials, materials that can be made biocompatible, metals such as stainless steel, titanium, polymers, Pebax (Pebax is a registered trademark of Ato Chimie Corporation of Allee des Vosges, Courbevoie, France), nylon, polyethylene, polyurethane, silicone, and any other material considered suitable for a particular application. Thus, a seeking device can be formed of the same material as the elongate member, or a material that is different than the elongate member. Examples of suitable structures considered suitable to form a seeking device include, but are not limited to, spheres, partial spheres, egg shaped structures, and any other structure considered suitable for a particular application. Alternatively, rounding off the material that forms an elongate member distal end can form a seeking device. Thus, an elongate member distal end can be round, or partially rounded.

While the elongate member 222 has been illustrated as having a particular structural configuration defining an inflation lumen and an elongate member curve, an elongate member can have any suitable structural configuration defining any suitable number of lumens and/or curves. Skilled artisans will be able to select a suitable structural configuration and number of lumens and/or curves to define on an elongate member according to a particular embodiment based on various considerations, including the procedure intended to be performed. Example number of lumens and/or curves considered suitable to include on an elongate member include, but are not limited to, one, at least one, two, a plurality, three, four, and any other number considered suitable for a particular application. For example, an elongate member body can optionally define a device lumen or a guide wire lumen adapted to receive a guide wire that extends from a first opening on elongate member proximal end to a second opening on elongate member distal end.

The balloon 224 can be formed of any suitable material and can be fabricated using any suitable method of manufacture, and skilled artisans will be able to select a suitable material to form a balloon and a suitable method of manufacture according to a particular embodiment based on various considerations, including the materials that form an elongate member. Example materials considered suitable to form a balloon include, but are not limited to, biocompatible materials, materials that can be made biocompatible, flexible materials, substantially flexible materials, polymers, Pebax (Pebax is a registered trademark of Ato Chimie Corporation of Allee des Vosges, Courbevoie, France), nylon, polyethylene, polyurethane, and any other material considered suitable for a particular application.

The balloon 224 can have any suitable structural arrangement, and skilled artisans will be able to select a suitable structural arrangement for a balloon according to a particular embodiment based on various considerations, including the structural arrangement of the passage wall being treated. For example, a balloon can have any suitable length and inflated balloon diameter. The inventors have determined that balloons that have a length between 1 centimeter and 3 centimeters, or between about 1 centimeter and about 3 centimeters, are considered suitable. In addition, the inventors have determined that balloons that have a length of 2 centimeters, or about 2 centimeters, are considered suitable. The inventors have also determined that balloons that have an inflated balloon diameter in the second inflated configuration between 1 millimeter and 9 millimeters, or between about 1 millimeter and about 9 millimeters, are considered suitable. In addition, the inventors have determined that balloons that have an inflated balloon diameter in the second inflated configuration between 3 millimeters and 7 millimeters, or between about 3 millimeters and about 7 millimeters, are considered suitable.

In the illustrated embodiment, the balloon 224 is attached to the elongate member 222 between the elongate member proximal end 226 and the elongate member distal end 228 at a balloon proximal junction 250 and a balloon distal junction 252. The balloon 224 comprises a balloon proximal end 254, a balloon distal end 256, and a balloon wall 258. The balloon wall 258 and the portion of the surface of the elongate member 222 disposed within the balloon 224 define a balloon chamber 260 that is adapted to receive a fluid such that the balloon 224 can be moved between a first deflated configuration and a second inflated configuration. In the deflated configuration the balloon 224 has a first outside diameter and in the inflated configuration the balloon 224 has a second outside diameter that is greater than the first outside diameter. FIG. 2 illustrates the balloon 224 in the first deflated configuration and FIG. 3 illustrates the balloon 224 in the second inflated configuration.

The balloon 224 is attached to the elongate member 222 such that the elongate member second opening 236 is in communication with the balloon chamber 260. With this structural arrangement, the balloon 224 is adapted to move between the first deflated configuration and second inflated configuration as fluid is moved into and out of the balloon chamber 260 via the inflation lumen 238 and the elongate member second opening 236.

The balloon proximal junction 250 and the balloon distal junction 252 can comprise any suitable method of attachment between the elongate member 222 and the balloon 224, and skilled artisans will be able to select a suitable method of attachment between a balloon and an elongate member according to a particular embodiment based on various considerations, including the materials that form the elongate member and balloon. Example methods of attachment considered suitable between an elongate member and a balloon include, but are not limited to, attachments formed by heat fusing, using adhesives, mechanical connections, and any other method considered suitable for a particular application.

A user inflates the balloon 224 by introducing a fluid, such as saline, into the inflation lumen 238 until the fluid passes through the elongate member second opening 236 and into the balloon chamber 260. The resulting pressure placed on the inner surface of the balloon wall 258 by the fluid causes the balloon 224 to inflate and adopt the second inflated configuration. To move the balloon 224 to the first deflated configuration, vacuum pressure can be applied to the inflation lumen 238 to remove fluid located within the balloon chamber 260 via the elongate member second opening 236, resulting in the balloon 224 collapsing and adopting the first deflated configuration.

Additional structure can be attached to the balloon catheter 220 to facilitate the inflation and deflation of the balloon 224, as described above. For example, an inflation device, such as a syringe, can be operatively connected, or attached, to the balloon catheter 220 (e.g., to elongate member proximal end 226) and adapted to move the balloon 224 between the first deflated configuration and second inflated configuration. For example, fluid can be introduced into a balloon chamber by applying a distally-directed force on a plunger associated with a conventional syringe. Alternatively, fluid can be removed from balloon chamber by applying a proximally-directed force on a plunger associated with a conventional syringe. Any inflation device capable of facilitating inflation and deflation of a balloon is considered suitable, and skilled artisans will be able to select a suitable inflation device according to a particular embodiment based on various considerations, including the procedure intended to be performed. Example inflation devices considered suitable include, but are not limited to, manually operated inflation devices, syringes, electromechanical inflation devices, pumps, and any other device considered suitable for a particular application.

Optionally, an elongate member can include one or more indicia disposed along its length. The one or more indicia can be formed on the outer surface of the elongate member, or be embedded within the material forming the elongate member. Alternatively, the one or more indicia can comprise a raised protuberance that extends outward and away from the elongate member body. Each indicia can extend about the entirety, or a portion, of the circumference of an elongate member. For example, one or more indicia can optionally be included on an elongate member to indicate the location of an elongate member curve. For example, a first indicia can be disposed at a location on the elongate member such that when the first indicia is located at, proximal to, or near, the cannula proximal end while a portion of the elongate member is disposed within the cannula lumen, the elongate member curve is free, or disposed outside of, the cannula lumen. A second indicia can be disposed distal to the first indicia at a location on the elongate member such that when the second indicia is located at, proximal to, or near, the cannula proximal end while a portion of the elongate member is disposed within the cannula lumen, a portion, or the entirety, of the elongate member curve disposed within the cannula lumen.

Alternative to, or in combination with, including one or more indicia to indicate the location of an elongate member curve, an elongate member can optionally include one or more indicia that indicate the location of a balloon. A first indicia can be disposed at a location on the elongate member such that when the first indicia is located at, proximal to, or near, the cannula proximal end while a portion of the elongate member is disposed within the cannula lumen, the balloon is free, or disposed outside of, the cannula lumen. A second indicia can be disposed distal to the first indicia at a location on the elongate member such that when the second indicia is located at, proximal to, or near, the cannula proximal end while a portion of the elongate member is disposed within the cannula lumen, the balloon distal end is disposed at, near, or proximal to, the cannula distal end.

Alternative to, or in combination with, including one or more indicia to indicate the location of an elongate member curve, and/or a balloon, an elongate member can optionally include one or more indicia disposed along its length that indicate the orientation of the elongate member curve and/or elongate member distal end. For example, a first indicia can be disposed along the elongate member length that correlates with the direction in which the elongate member curve and/or elongate member distal end will extend when free of, or outside of, the cannula lumen.

Step 106 can be accomplished by applying a distally-directed force on any suitable portion of the cannula 200 such that the cannula 200 is advanced toward a point of treatment. This step can be accomplished with the assistance of direct visualization of the cannula (e.g., scope), transcutaneously, transillumination techniques (e.g., an optical fiber is disposed within a lumen defined by an elongate member, embedded within the material that forms the elongate member, or is attached to the outer surface of an elongate member and is attached to a light source), a camera, or any other suitable visualization technique.

An optional step comprises confirming placement of the cannula 200 at a point of treatment. This step can be accomplished using direct visualization (e.g., scope), transcutaneously, transillumination techniques, a camera, or any other suitable visualization technique. Optionally, the cannula 200 can be positioned proximal to, distal to, at, or near, a point of treatment.

Step 108 can be accomplished by applying a distally-directed force on any suitable portion of the balloon catheter 220 such that it is advanced distally through the cannula lumen 212 and the portion of the elongate member 222 that defines the elongate member curve 240 is free of, or disposed outside of, the cannula lumen 212 and the elongate member 222 moves from the first configuration to the second curved configuration. Thus, the portion of the elongate member 222 that defines elongate member curve 240 is disposed distal to cannula distal end 204. This step is considered advantageous at least because the structural arrangement of the elongate member 222 (e.g., curved relative to the cannula 200) provides a mechanism for locating an opening defined by a passage wall without requiring the guidance of a previously placed guide wire. Thus, any of the steps described herein can be accomplished without a previously placed guide wire.

Alternatively, step 108 can comprise advancing the elongate member 222 through the cannula lumen 212 such that a portion of the elongate member 222 that defines the elongate member curve 240 is disposed distal to cannula distal end 204 and is free of, or outside of, the cannula lumen 212. This moves the elongate member 222 from the first straight, or substantially straight configuration, to a configuration between the straight, or substantially straight configuration, and the curved configuration. The completion of this alternative step is considered advantageous in bodily passages that do not require an entire elongate member curve to be advanced from a cannula lumen to complete a procedure or locate a point of treatment (e.g., opening defined by a passage wall).

An optional step comprises confirming that the portion the elongate member 222 that defines the elongate member curve 240 is free of the cannula lumen 212. This step can be accomplished using direct visualization (e.g., scope), transcutaneously, transillumination techniques, a camera, locating one of one or more indicia on the elongate member, or any other suitable visualization technique.

Optionally, a portion, or the entirety, of a cannula and/or elongate member (e.g., elongate member distal end, elongate member distal tip), or a distal tip of an elongate member, can be formed of, or include, a radiopaque material such that the location, orientation, and/or length of elongate member disposed distal to a cannula can be determined using fluoroscopy, or x-ray. The radiopaque material can be added in any fabrication method or absorbed into, or sprayed onto, the surface of the entirety, or a portion, of the cannula and/or elongate member. Any suitable radiopaque material can be used including, but not limited to, barium sulfate, bismuth subcarbonate, zirconium dioxide, cadmium, tungsten, gold, tantalum, bismuth, platinum, iridium, and rhodium.

Step 110 can be accomplished by advancing the cannula 200 and/or the elongate member 222 toward the opening defined by the passage wall (e.g., applying a force on an axis that passes through the elongate member lengthwise axis or first axis). This step can be accomplished using tactile feedback of the placement of the elongate member 222 within the bodily passage (e.g., within the opening defined by the passage wall) or visualizing the elongate member 222 using direct visualization (e.g., scope), transcutaneously, transillumination techniques, a camera, or any other suitable visualization technique. For example, once the elongate member distal end 228 has located the opening defined by the passage wall, a portion of the elongate member 222 can be passed through, or into, the opening such that a user will have tactile feedback as to the positioning of the elongate member distal end 228 within, or through, the opening.

An optional step comprises rotating the balloon catheter 220 (e.g., elongate member 222) such that the elongate member distal end 228 is positioned at, or directed toward, the opening defined by the passage wall. This step can be accomplished by applying torque to a portion of the cannula 202 and/or the elongate member 222 (e.g., about the lengthwise axis of the elongate member 222) when the elongate member curve 240 is disposed distal to the cannula distal end 204.

Another optional step comprises determining if the elongate member distal end is disposed through the opening. This step can be accomplished using direct visualization (e.g., scope), transcutaneously, transillumination techniques, a camera, tactile feedback, or using any other suitable visualization technique.

Step 112 can be accomplished by applying a distally-directed force on any suitable portion of the elongate member 222 such that the balloon 224 passes through the cannula lumen 212 and is disposed distal to the cannula distal end 204 and within the opening defined by the passage wall.

An optional step comprises confirming placement of the balloon 224 within the opening defined by the passage wall. This step can be accomplished using direct visualization (e.g., scope), transcutaneously, transillumination techniques, a camera, radiopaque material, or using any other suitable visualization technique.

Another optional step comprises advancing the balloon 242 distal to, or past, the opening defined by the passage wall. This step is considered advantageous at least because it provides a method of performing treatment on the tissue of passage walls that define a bodily passages, such as a sinus cavity, that are distal to, or past, an opening defined by the passage wall (e.g., an ostium).

Alternative to completing the steps of navigating the elongate member distal end 228 toward the opening defined by the passage wall and advancing the elongate member distal end 228 through the opening defined by the passage wall, a step comprising advancing the elongate member distal end 228 through a portion of the bodily passage can be completed. This alternative step is considered advantageous at least because it provides a mechanism for advancing an elongate member 222 and a portion, or the entirety of, the elongate member curve 240 through the tortuous anatomy of a bodily passage such that the tissue of a passage wall defining the bodily passage can be treated. This step can be accomplished by applying a distally-directed force on any suitable portion of an elongate member 222 such that elongate member curve 240, or a portion of elongate member curve 240, is disposed distal to cannula distal end 204.

Step 114 can be accomplished by passing a fluid through the inflation lumen 238 and into the balloon chamber 260 to move the balloon 224 from its first deflated configuration toward its second inflated configuration, or to its second inflated configuration. For example, a syringe in communication with the inflation lumen 238 can be used to introduce the fluid into the balloon chamber 260 by applying a distally-directed force on the plunger of the syringe. The amount of the exterior surface of the balloon 224 that contacts the tissue in the passage wall, and the amount of pressure exerted by the exterior surface of the balloon 224 onto the tissue in the passage wall, will depend on the amount of fluid introduced into the balloon chamber 260. An optional step comprises continuing the step of passing a fluid through the inflation lumen 238 and into the balloon chamber 260 until the balloon 224 contacts and dilates the opening defined by the passage wall.

Example fluids considered suitable to pass through an inflation lumen 238 and into a balloon chamber 260 include, but are not limited to, saline, water contrast, a mixture of one or more of saline, water, and/or contrast, and any other fluid considered suitable for a particular application.

Step 116 can be accomplished by stopping the step of passing fluid through the inflation lumen 238 and into the balloon chamber 260. This can be accomplished, for example, by stopping the application of the distally-directed force on the plunger of the syringe.

Step 118 can be accomplished by removing the fluid, or a portion of the fluid, passed into the balloon chamber 260 to move the balloon 224 toward the first deflated configuration. For example, a syringe in communication with the inflation lumen 238 can be used to provide vacuum pressure to remove the fluid, or a portion of the fluid, from the balloon chamber 260 by applying a proximally-directed force on the plunger of the syringe. The amount of fluid removed from the balloon chamber 260 can vary depending on the procedure. For example alternative to removing a portion of the fluid, all of the fluid, or substantially all of the fluid, can be removed from the balloon chamber 260.

Step 120 can be accomplished by applying a proximally-directed force on any suitable portion of the elongate member 222 such that the elongate member 222 is withdrawn from the opening defined by the passage wall.

Step 122 can be accomplished by applying a proximally-directed force on any suitable portion of the elongate member 222 such that the elongate member 222 is withdrawn from the cannula lumen 212. Optionally, this step can be omitted from method 100.

Step 124 can be accomplished by applying a proximally-directed force on any suitable portion of the cannula 200 such that the cannula 200 is removed from the bodily passage.

While step 120, step 122, and step 124 have been described as separate steps, step 120, step 122, and step 124 can be accomplished concurrently with one another, or combined in any other suitable manner. For example, step 120 and step 122 can be accomplished concurrently, or step 122 and step 124 can be accomplished concurrently.

While an exemplary balloon catheter 220 has been illustrated as accomplishing method 100, any suitable medical device can be used to accomplish the methods described herein. Skilled artisans will be able to select a suitable medical device to accomplish one or more steps described herein according to a particular embodiment based on various considerations, including the procedure intended to be performed. For example, an irrigation catheter having an elongate member that defines a curve when it is free of, or outside of, a cannula lumen, as described with respect to elongate member 222, or any other medical device having an elongate member that defines a curve when it is free of, or outside of, a cannula lumen, as described with respect to elongate member 222, can be used to complete one or more steps and/or methods described herein. Alternatively, a medical device having an elongate member that defines a curve, as described with respect to elongate member 222, can be advanced free of a cannula into a bodily passage.

It is considered advantageous to complete method 100 in the order illustrated and/or described. It is noted, however, that any order is considered suitable.

While various steps, alternative steps, and optional steps have been described above with respect to treating tissue in a passage wall defining a bodily passage, these steps, alternative steps, and optional steps can be included in, accomplished concurrently with, and/or accomplished in the alternative to, the methods, steps, alternative steps, and/or optional steps described below with respect to treating tissue in a passage wall defining a bodily passage and/or treating tissue in a passage wall defining a sinus passage.

Figure 4:
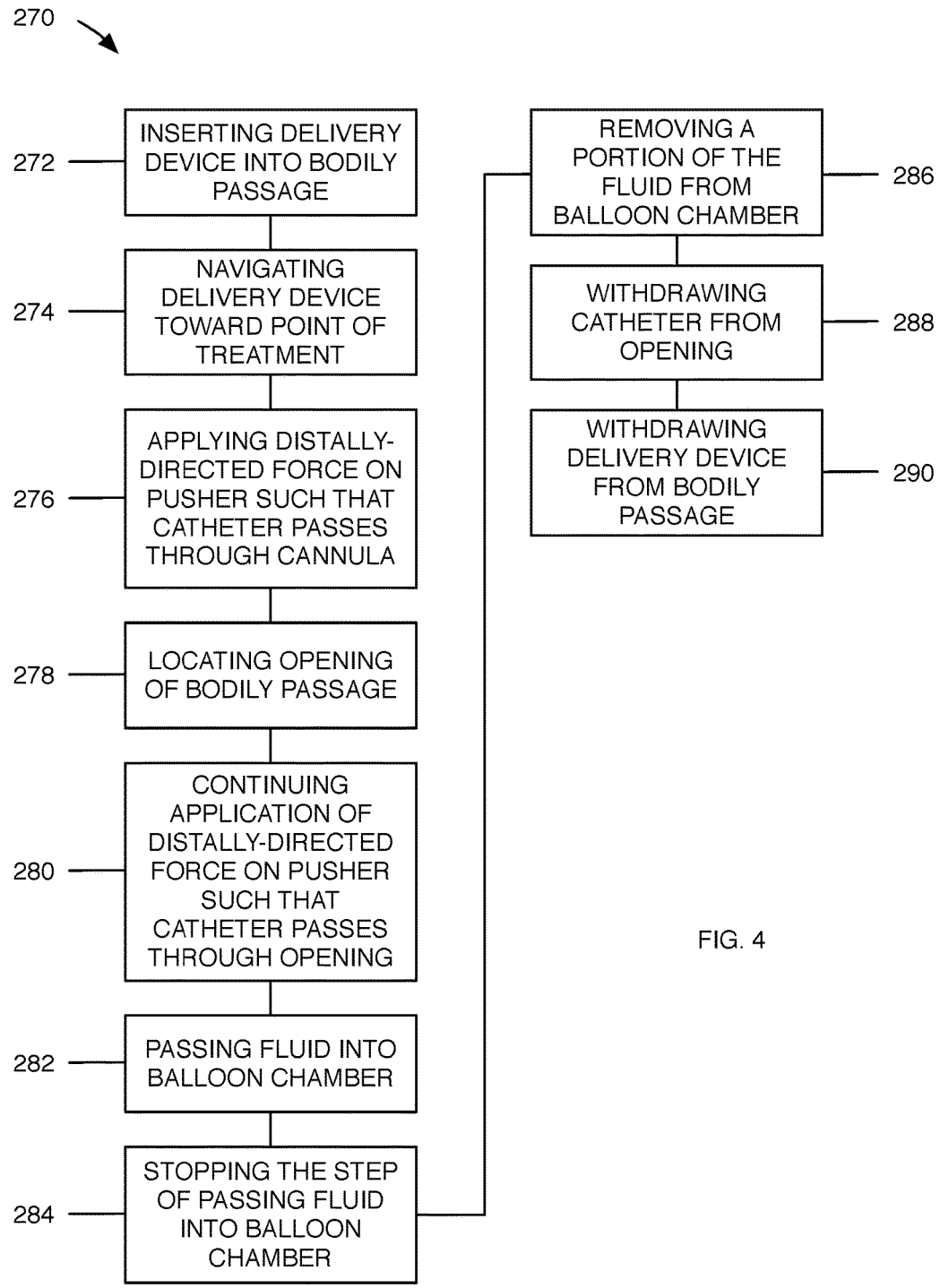
FIG. 4 is a flowchart representation of another exemplary method of treating tissue in a wall defining a bodily passage.

FIG. 4 is a flowchart representation of another exemplary method 270 of treating tissue in a passage wall defining a bodily passage.

A step 272 comprises inserting a delivery device having a delivery device proximal end and a delivery device distal end into a bodily passage such that the delivery device distal end is disposed within the bodily passage. The delivery device comprising a housing, cannula, pusher, and a catheter. The housing having a housing proximal end, housing distal end, and a housing body defining a housing lumen. The cannula having a cannula proximal end attached to the housing, a cannula distal end, and a cannula body defining a cannula lumen in communication with the housing lumen. The pusher slidably disposed within the housing lumen and having a pusher proximal end, pusher distal end, and a pusher body defining a pusher lumen. The catheter comprising an elongate member and balloon. The elongate member having an elongate member proximal end attached to the pusher, elongate member distal end disposed within the cannula lumen, elongate member length, and an elongate member body that defines an inflation lumen and an elongate member curve. The inflation lumen is in communication with the pusher lumen. The elongate member length extends from the elongate member proximal end to the elongate member distal end. The elongate member curve is defined along a portion of the elongate member. The elongate member is adapted to move between a first straight, or substantially straight, configuration in which the portion of the elongate member that defines elongate member curve is straight, or substantially straight, when disposed within the cannula lumen and a second curved configuration in which the portion of elongate member that defines the elongate member curve is curved when free of, or outside of, the cannula lumen. The balloon is disposed on the elongate member and has a balloon wall that defines a balloon chamber in communication with the inflation lumen. The balloon is moveable between a first deflated configuration and a second inflated configuration as fluid is moved into and out of the balloon chamber. Another step 274 comprises navigating the delivery device distal end toward a point of treatment within the bodily passage. The point of treatment comprises an opening defined by the wall of the bodily passage. Another step 276 comprises applying a distally-directed force on the pusher such that the catheter passes through the cannula lumen, the portion of the elongate member that defines the elongate member curve is free of the cannula lumen, and the elongate member moves from the first straight, or substantially straight configuration, to the second curved configuration. Another step 278 comprises locating the opening of the bodily passage. Another step 280 comprises continuing the application of distally-directed force on the pusher such that the catheter distal end passes through the opening. Another step 282 comprises passing a fluid through the pusher lumen and inflation lumen and into the balloon chamber to move the balloon from the first deflated configuration toward the second inflated configuration. Another step 284 comprises stopping the step of passing a fluid through the pusher lumen and inflation lumen and into the balloon chamber. Another step 286 comprises removing a portion of the fluid from the balloon chamber. Another step 288 comprises withdrawing the catheter from the opening. Another step 290 comprises withdrawing the delivery device from the bodily passage.

Figure 5:
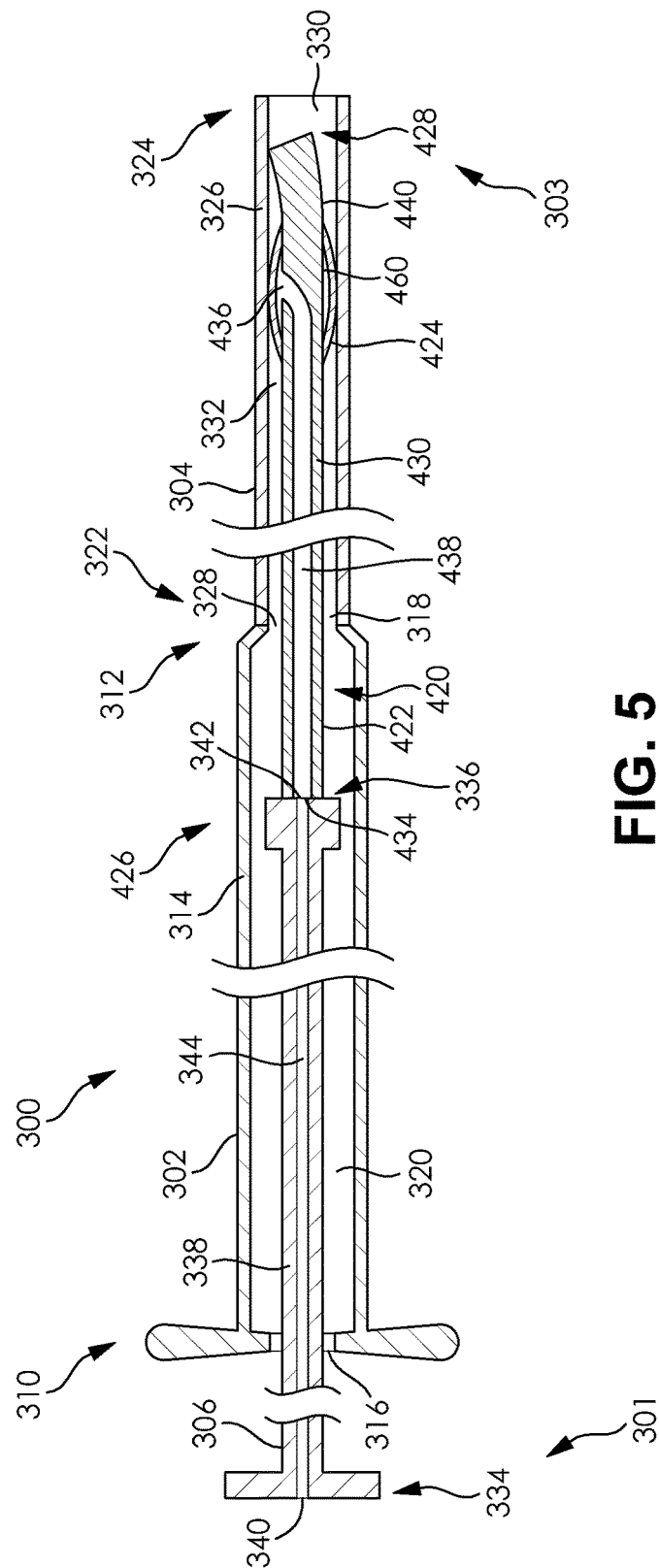
FIG. 5 is a sectional view of an exemplary delivery device.

Step 272 can be accomplished by applying a distally-directed force on any suitable portion of a delivery device such that the delivery device distal end is disposed within the bodily passage (e.g., through an opening defined by a passage wall). Any suitable delivery device having any suitable structural arrangement can be used to accomplish step 272, and skilled artisans will be able to select a suitable delivery device and structural arrangement for a delivery device according to a particular embodiment based on various considerations, including the tissue desired to be treated. FIG. 5 illustrates an exemplary delivery device 300 for accomplishing one or more of the steps, and/or methods, described herein. The delivery device 300 has a delivery device proximal end 301, a delivery device distal end 303, and comprises a housing 302, a cannula 304, a pusher 306, and a catheter 420.

The housing 302 has a housing proximal end 310, a housing distal end 312, and a housing body 314 that defines a first housing opening 316, a second housing opening 318, and a housing lumen 320. The housing lumen 320 extends from the first housing opening 316 to the second housing opening 318.

The housing 302 can be formed of any suitable material and have any suitable structural arrangement, and skilled artisans will be able to select a suitable material to form a housing and a suitable structural arrangement for a housing according to a particular embodiment based on various considerations, including the desired bodily passage within which a catheter is to be utilized. Example materials considered suitable to form a housing include, but are not limited to, biocompatible materials, materials that can be made biocompatible, polymers, such as nylon, polyethylene, and polycarbonate, a mixture thereof, or any other material considered suitable for a particular application.

The housing 302 can be fabricated using any suitable method of manufacture, and skilled artisans will be able to select a suitable method of manufacture to fabricate a housing according to a particular embodiment based on various considerations, including the material that forms the housing. Example methods of manufacture considered suitable to fabricate a housing considered suitable include, but are not limited to, injection molding, and any other method of manufacture considered suitable for a particular application.

The cannula 304 has a cannula proximal end 322, a cannula distal end 324, and a cannula body 326 that defines a first cannula opening 328, a second cannula opening 330, and a cannula lumen 332. The cannula lumen 332 extends from the first cannula opening 328 to the second cannula opening 330. The cannula proximal end 322 is attached to the housing distal end 312 such that the housing lumen 320 and the cannula lumen 332 are in communication.

In the illustrated embodiment, the cannula 304 is rigid, or substantially rigid, relative to the catheter 420, or a portion of the catheter 420, and can be formed of any suitable material, and skilled artisans will be able to select a suitable material to form a cannula according to a particular embodiment based on various considerations, including the desired bodily passage within which a catheter is to be deployed. Example materials considered suitable to form a cannula include, but are not limited to, biocompatible materials, materials that can be made biocompatible, metals such as stainless steel, titanium, nitinol, cobalt chromium, polymers, Pebax (Pebax is a registered trademark of Ato Chimie Corporation of Allee des Vosges, Courbevoie, France), nylon, polyethylene, polyurethane, silicone, coiled materials, braided materials, and any other material considered suitable for a particular application. Alternatively, a cannula can be formed of the same material as a catheter such that the cannula and catheter have the same rigidity or flexibility.

The pusher 306 has a pusher proximal end 334, a pusher distal end 336 disposed within the housing lumen 320, a pusher body 338, and a pusher length that extends from the pusher proximal end 334 to the pusher distal end 336. The pusher body 338 defines a first pusher opening 340, a second pusher opening 342, and a pusher lumen 344 that extends from the first pusher opening 340 to the second pusher opening 342. The pusher distal end 336 is slidably disposed within the housing lumen 320 (e.g., when the pusher 306 is in the first configuration). However, alternative embodiments can include a pusher 306 that has a distal end 336 that is disposed in the cannula lumen 332, or between the housing 302 and the cannula 304, when the pusher 306 is in the first configuration).

The pusher 306 (e.g., pusher proximal end 334) can include any suitable structural arrangement, connector, and/or adapter capable of attaching, or assisting with attaching, one or more devices (e.g., syringe, inflation device) to the pusher 306 such that the attached device is in communication with the pusher lumen 344 and the balloon chamber 460 via the first pusher opening 340, as described in more detail herein. Skilled artisans will be able to select a suitable structural arrangement, connector, and/or adapter to include on a pusher according to a particular embodiment based on various considerations, including the materials that form the pusher. Example structural arrangements, connectors, and/or adapters considered suitable to include on a pusher include, but are not limited to, threads, threaded connectors, Tuohy Borst adapters, luer lock connectors, and any other structural arrangement, connector, and/or adapter considered suitable for a particular application.

The pusher 306 can be formed of any suitable material and fabricated using any suitable method of manufacture, and skilled artisans will be able to select a suitable material to form a pusher and a suitable method of manufacture to fabricate a pusher according to a particular embodiment based on various considerations, such as the material that forms the housing of a delivery device. Example materials considered suitable to form a pusher include, but are not limited to, biocompatible materials, materials that can be made biocompatible, metals, such as stainless steel, titanium, plastics, such as nylon, polyethylene, high-density polyethylene, and any other material considered suitable for a particular application.

The catheter 420 is similar to the catheter 220 illustrated in FIGS. 2 and 3 and described above, except as detailed below. Reference numbers in FIG. 4 refer to the same structural element or feature referenced by the same number in FIGS. 2 and 3, offset by 200. Thus, catheter 420 comprises an elongate member 422 and a balloon 424.

In the illustrated embodiment, the elongate member 422 is operatively connected, or attached to, the pusher 306 such that the inflation lumen 438 is in communication with the pusher lumen 344. Attachment of the elongate member 422 to the pusher 306 can be accomplished using any suitable method of attachment, and skilled artisans will be able to select a suitable method of attachment according to a particular embodiment based on various considerations, such as the bodily passage within which a catheter is intended to be deployed. Example methods of attachment considered suitable between an elongate member and pusher include, but are not limited to, insert molding, using an adhesive, heat fusing, welding, threaded connections, mechanical connections, and any other method of attachment considered suitable for a particular application.

The pusher 306 has a pusher first configuration and a pusher second configuration. In the first configuration, the pusher distal end 336 is positioned such that at least a portion of, or the entirety of, the elongate member 422 is disposed within the cannula lumen 332. In the illustrated embodiment, when the pusher 306 is in the pusher first configuration, the portion of the elongate member 422 that defines the elongate member curve 440 is disposed within the cannula lumen 332. Thus, when the pusher 306 is in the pusher first configuration, the elongate member 422 is in the straight, or substantially straight, configuration and the elongate member distal end 428 is disposed within the cannula lumen 332. In the pusher second configuration, the pusher distal end 336 is advanced distally (e.g., by applying distally-directed force on pusher proximal end 334) and positioned such that the portion of the elongate member 422 that defines the elongate member curve 440 is disposed distal to the cannula distal end 324. Thus, when the pusher 306 is in the pusher second configuration, the elongate member 422 is in the second curved configuration.

While an exemplary catheter 420 has been illustrated as being operatively connected, or attached, to the pusher 306, any suitable catheter, or medical device, can be operatively connected, or attached, to a pusher, such that it is disposed within a cannula, as described herein. Skilled artisans will be able to select a suitable medical device to accomplish one or more steps described herein according to a particular embodiment based on various considerations, including the procedure intended to be performed. Example catheters and/or medical devices considered suitable to operatively connect, or attach, to a pusher and position within a cannula lumen include, but are not limited to, irrigation catheters having an elongate member that defines a curve when it is free of, or outside of, a cannula lumen (e.g., as described with respect to elongate member 422), elongate members that define a curve when it is free of, or outside of, a cannula lumen (e.g., as described with respect to elongate member 422), balloon catheters having an elongate member that defines a curve when it is free of, or outside of, a cannula lumen (e.g., as described with respect to elongate member 422), and any other medical device having an elongate member that defines a curve when it is free of, or outside of, a cannula lumen (e.g., as described with respect to elongate member 422) considered suitable for a particular application. For example, alternative to an elongate member defining an inflation lumen and having a balloon disposed along its length, an elongate member attached to a pusher and having an elongate member curve, as described herein, can define an irrigation lumen (e.g., that extends from an opening on the proximal end of the elongate member to an opening on the distal end of the elongate member) and/or suction lumen (e.g., that extends from an opening on the proximal end of the elongate member to an opening at the distal end of the elongate member) for introducing and/or removing material from a bodily passage, sinus passage, airway, sinus cavity, the urinary tract, or any other suitable bodily passage. Optionally, a pusher and/or an elongate member attached to the pusher can omit the inclusion of a lumen.

While the catheter 420 has been illustrated as being disposed within the cannula lumen 332 and the elongate member 422 has been described as straight, or substantially straight, when the pusher 306 is in the pusher first configuration, any suitable length of a catheter can be disposed within a cannula lumen when a pusher is in the pusher first configuration, and skilled artisans will be able to select a suitable length of a catheter to position within a cannula lumen according to a particular embodiment based on various considerations, such as the bodily passage within which the catheter is intended to be deployed. Example lengths of a catheter considered suitable to position within a cannula lumen when a pusher is in a pusher first configuration include, but are not limited to, at least a portion of a catheter (e.g., elongate member), the entire length of a catheter (e.g., elongate member), the portion of the catheter (e.g., elongate member) proximal to a curve, the portion of the catheter (e.g., elongate member) distal to a curve, such that a portion of the curve is disposed within the cannula lumen, such that a portion of the curve is disposed distal to the cannula, and any other length considered suitable for a particular application.

Step 274 can be accomplished by applying a distally-directed force on any suitable portion of delivery device 300 (e.g., housing 302, pusher 306) such that the delivery device distal end 301 is advanced toward a point of treatment. This step can be accomplished with the assistance of direct visualization of the cannula (e.g., scope), transcutaneously, transillumination techniques, using a camera, or any other suitable visualization technique.

While the point of treatment has been described as an opening defined by the passage wall, the delivery devices, cannulas, and/or catheters described herein can be used to treat the tissue in a wall defining any suitable bodily passage or opening. Skilled artisans will be able to select a suitable tissue for treatment with a particular delivery device, catheter, and/or cannula based on various considerations, including the nature of the treatment intended to be performed. Examples of other tissues considered suitable to treat using a delivery device, catheter, and/or cannula, such as those described herein, include, but are not limited to, the tissue of a passage wall defining a bodily passage, an opening defined by a passage wall, tissue in a passage wall that defines a sinus passage, tissue in a passage wall that defines an ostium, tissue in a passage wall that defines a sinus cavity, tissue in a passage wall that defines an airway, tissue in a passage wall that defines the urinary tract, and any other tissue considered suitable for a particular application.

Step 276 can be accomplished by applying a distally-directed force on any suitable portion of pusher 306 and maintaining the position of the housing 302, advancing housing 302 in a proximal direction (e.g., by applying a proximally-directed force on any suitable portion of the housing 302) while maintaining the position of pusher 306, or advancing pusher 306 in a distal direction relative to the housing 302. This step is considered advantageous at least because the structural arrangement of the elongate member 422 (e.g., curved relative to the cannula 304) provides a mechanism for locating an opening defined by a passage wall without requiring the guidance of a previously placed guide wire. Thus, any of the steps described herein can be accomplished without a previously placed guide wire.

Step 276 is accomplished such that the elongate member 422 is advanced through the cannula lumen 412 and the portion of the elongate member 422 that defines the elongate member curve 440 is free of, or outside of, the cannula lumen 332 and the elongate member 422 moves from the first configuration to the second curved configuration. Thus, the portion of the elongate member 422 that defines elongate member curve 440 is disposed distal to the cannula distal end 324.

Alternatively, step 276 can comprise advancing the pusher 306 such that a portion of the elongate member 422 that defines the elongate member curve 440 is disposed distal to cannula distal end 324 and free of, or outside of, the cannula lumen 332 and the elongate member 422 moves from the first straight, or substantially straight configuration, to a configuration between the straight, or substantially straight configuration, and the curved configuration. The completion of this alternative step is considered advantageous in bodily passages that do not require an entire elongate member curve to be advanced from a cannula lumen to complete a procedure or locate a point of treatment (e.g., opening defined by a passage wall).

Step 278 can be accomplished by advancing the delivery device 300 toward the opening defined by the passage wall (e.g., by applying a force along an axis that passes through elongate member first axis 442 on any suitable portion of the delivery device). Tactile feedback will be provided to the user of the delivery device 300 once the opening defined by the passage wall has been located (e.g., the elongate member distal end 428 will enter, or pass through, the opening). These steps are considered advantageous at least because they can be accomplished without a visualization device. Alternatively, step 278 can be accomplished using direct visualization of the elongate member (e.g., scope), transcutaneously, transillumination techniques, using a camera, or any other suitable visualization technique independent of, or in combination with, tactile feedback. An optional step comprises applying torque to any suitable portion the delivery device (e.g., pusher 306, housing 302, cannula 304) to cause the elongate member distal end 428 to rotate relative to the cannula 304.

Step 280 can be accomplished by continuing the application of a distally-directed force on any suitable portion of the pusher 306 and maintaining the position of the housing 302, advancing the housing 302 in a proximal direction (e.g., by applying a proximally-directed force on any suitable portion of the housing 302) while maintaining the position of the pusher 306, or advancing the pusher 306 in a distal direction (e.g., in combination with the housing 302), until the elongate member distal end 428 passes through the opening defined by the passage wall. This step can be accomplished with the assistance of direct visualization of the elongate member 422 (e.g., scope), transcutaneously, transillumination techniques, using a camera, or any other suitable visualization technique.

The length of the catheter 420 passed through the opening defined by the passage wall will depend on the procedure intended to be completed. For example, the catheter 420 can be passed through the opening such that the balloon 424, or a portion of the balloon 424, is positioned within, distal to, beyond, or proximal to the opening. Alternatively, in procedures in which the tissue in a wall defining a bodily passage is being treated, step 280 comprises continuing the application of distally-directed force on the pusher 306 such that the catheter 420 is advanced through the second cannula opening 330 and the balloon 424 is passed through the second cannula opening 330 and into the bodily passage.

Step 282 can be accomplished by passing a fluid through the pusher lumen 344 and the inflation lumen 438 and into the balloon chamber 460 to move the balloon 424 from its first deflated configuration toward its second inflated configuration. For example, a syringe in communication with the pusher lumen 344 and the inflation lumen 438 can be used to introduce the fluid into the balloon chamber 460. The amount of the exterior surface of the balloon 424 that contacts the tissue in the passage wall, and the amount of pressure exerted by the exterior surface of the balloon 424 onto the tissue in the passage wall, will depend on the amount of fluid introduced into the balloon chamber 460. Examples of fluids considered suitable to pass through an inflation lumen and into a balloon chamber are described above.

Step 284 can be accomplished by stopping the step of passing fluid through the pusher lumen 344 and the inflation lumen 438 and into the balloon chamber 460. This can be accomplished, for example, by stopping the application of the distally-directed force on the plunger of the syringe.

Step 286 can be accomplished by removing the fluid, or a portion of the fluid, passed into the balloon chamber 460. For example, a syringe in fluid communication with the pusher lumen 344 and the inflation lumen 438 can be used to provide vacuum pressure to remove the fluid, or a portion of the fluid, from the balloon chamber 460. The amount of fluid removed from the balloon chamber 460 can vary depending on the procedure. For example alternative to removing a portion of the fluid, all of the fluid, or substantially all of the fluid, can be removed from the balloon chamber 460.

Step 288 can be accomplished by applying a proximally-directed force on any suitable portion of pusher 306 and maintaining the position of the housing 302, advancing housing 302 in a distal direction (e.g., by applying a distally-directed force on any suitable portion of the housing 302) while maintaining the position of pusher 306 relative to the housing 302, or advancing pusher 306 in a proximal direction relative to the housing 302.

Step 290 can be accomplished by applying a proximally-directed force on any suitable portion of the delivery device 300 such that the delivery device 300 is withdrawn from the bodily passage.

While step 288 and step 290 have been described as separate steps, step 288 and step 290 can be accomplished concurrently with one another.

It is considered advantageous to complete method 270 in the order illustrated and/or described. It is noted, however, that any order is considered suitable.

While various steps, alternative steps, and optional steps have been described above with respect to treating tissue in a passage wall defining a bodily passage, these steps, alternative steps, and optional steps can be included in, accomplished concurrently with, and/or accomplished in the alternative to, the methods, steps, alternative steps, and/or optional steps described above and/or below with respect to treating tissue in a passage wall defining a bodily passage and/or with respect to treating tissue in a passage wall defining a sinus passage.

Figure 6:
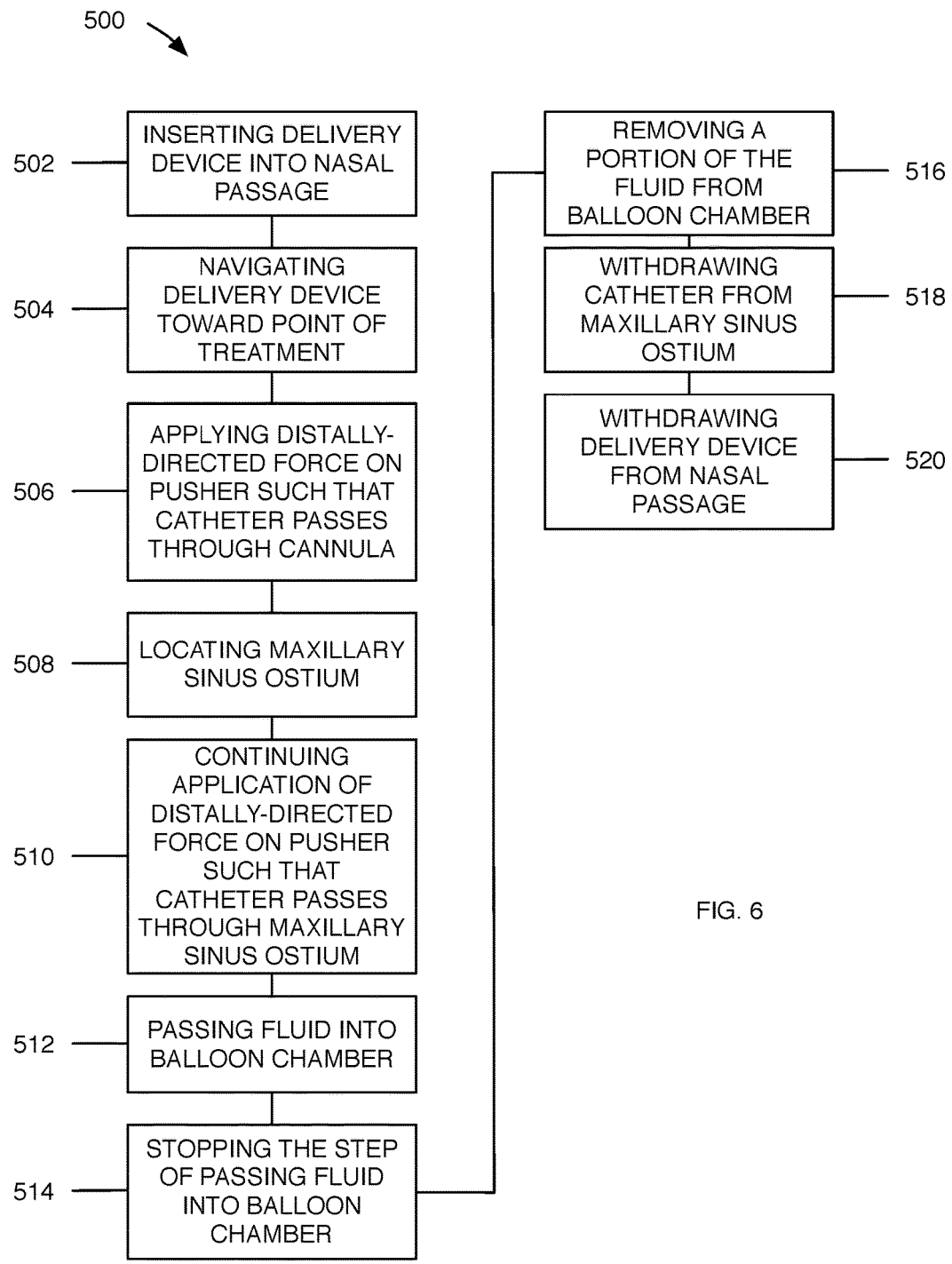
FIG. 6 is a flowchart representation of another exemplary method of treating tissue in a wall defining a bodily passage.

FIG. 6 is a flowchart representation of an exemplary method 500 of treating tissue in a passage wall defining a sinus passage.

A step 502 comprises inserting a delivery device having a delivery device proximal end and a delivery device distal end into a nasal passage such that the delivery device distal end is disposed within the nasal passage. The delivery device comprising a housing, cannula, pusher, and a catheter. The housing having a housing proximal end, housing distal end, and a housing body defining a housing lumen. The cannula having a cannula proximal end attached to the housing, a cannula distal end, and a cannula body defining a cannula lumen in communication with the housing lumen. The pusher slidably disposed within the housing lumen and having a pusher proximal end, pusher distal end, and a pusher body defining a pusher lumen. The catheter comprising an elongate member and balloon. The elongate member having an elongate member proximal end attached to the pusher, elongate member distal end disposed within the cannula lumen, elongate member length, and an elongate member body that defines an inflation lumen and an elongate member curve. The inflation lumen in communication with the pusher lumen. The elongate member length extends from the elongate member proximal end to the elongate member distal end. The elongate member curve is defined along a portion of the elongate member. The elongate member is adapted to move between a first straight, or substantially straight, configuration in which the portion of the elongate member that defines elongate member curve is straight, or substantially straight, when disposed within the cannula lumen and a second curved configuration in which the portion of elongate member that defines the elongate member curve is curved when free of, or outside of, the cannula lumen. The balloon is disposed on the elongate member and has a balloon wall that defines a balloon chamber in communication with the inflation lumen. The balloon is moveable between a first deflated configuration and a second inflated configuration as fluid is moved into and out of the balloon chamber. Another step 504 comprises navigating the delivery device distal end toward a point of treatment. The point of treatment comprising a maxillary sinus ostium defined by a sinus passage wall. Another step 506 comprises applying a distally-directed force on the pusher such that the catheter passes through the cannula lumen and the portion of the elongate member that defines the elongate member curve is free of, or outside of, the cannula lumen and the elongate member moves from the first straight, or substantially straight configuration, to the second curved configuration. Another step 508 comprises locating the maxillary sinus ostium. Another step 510 comprises continuing the application of distally-directed force on the pusher such that the catheter passes through the maxillary sinus ostium. Another step 512 comprises passing a fluid through the pusher lumen and inflation lumen and into the balloon chamber to move the balloon from the first deflated configuration toward the second inflated configuration. Another step 514 comprises stopping the step of passing fluid through the pusher lumen and inflation lumen and into the balloon chamber. Another step 516 comprises removing a portion of the fluid from the balloon chamber. Another step 518 comprises withdrawing the catheter from the maxillary sinus ostium. Another step 520 comprises withdrawing the delivery device from the nasal passage.

Step 502 can be accomplished by applying a distally-directed force on any suitable portion of a delivery device such that the delivery device distal end is disposed within the nasal passage. Any suitable delivery device having any suitable structural arrangement can be used to accomplish step 502, and skilled artisans will be able to select a suitable delivery device and structural arrangement for a delivery device according to a particular embodiment based on various considerations, including the bodily passage desired to be treated. An exemplary delivery device 300 for accomplishing one or more of the steps, and/or methods, described herein is illustrated in FIG. 5. The delivery device 300 has a delivery device proximal end 301, a delivery device distal end 303, and comprises a housing 302, a cannula 304, a pusher 306, and a catheter 420.

Step 504 can be accomplished by applying a distally-directed force on any suitable portion of delivery device 300 such that the delivery device distal end 303 is advanced toward a point of treatment. This step can be accomplished with the assistance of direct visualization of the cannula (e.g., scope), transcutaneously, transillumination techniques, using a camera, or any other suitable visualization technique.

Figure 6A:
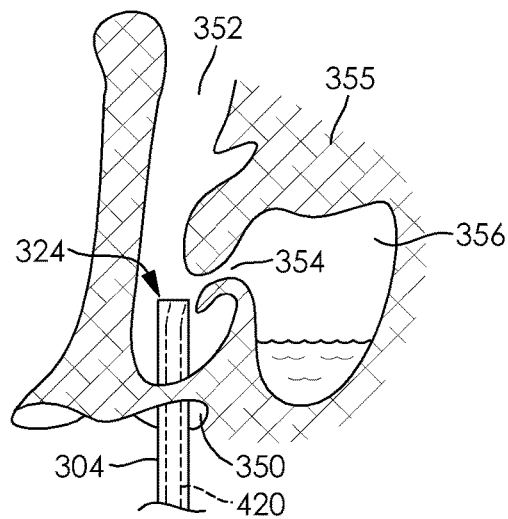
FIG. 6A is a partial sectional view of a patient with the delivery device illustrated in FIG. 5 partially disposed in a nasal passage. The elongate member is in the first straight, or substantially straight, configuration.
Figure 6B:
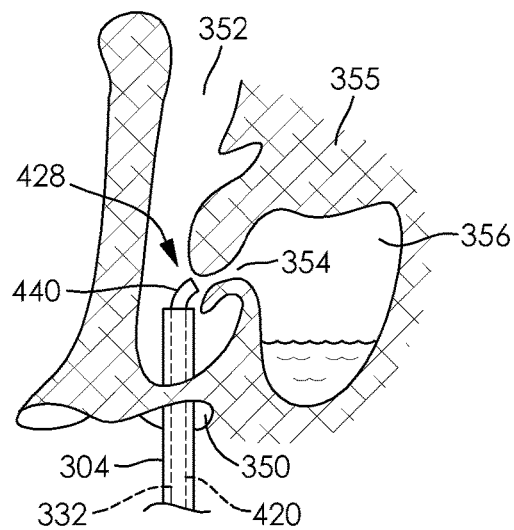
FIG. 6B is a partial sectional view of a patient with the delivery device illustrated in FIG. 5 partially disposed in a nasal passage in a partially deployed configuration. The elongate member is in the second curved configuration.

FIGS. 6A, 6B, 6C, and 6D illustrate the treatment of a bodily passage using delivery device 300. FIG. 6A illustrates the delivery device distal end 303 passed through nostril 350 and disposed within a nasal passage 352. The delivery device 300 has been advanced toward a point of treatment. In the illustrated embodiment, the point of treatment is the maxillary sinus ostium 354 defined by the sinus passage wall 355. The maxillary sinus ostium 354 provides access to the maxillary sinus cavity 356. In FIGS. 6A and 6B, the maxillary sinus ostium 354 is blocked preventing material within the maxillary sinus cavity 356 from draining and air from circulating throughout the maxillary sinus cavity 356.

Step 506 can be accomplished by applying a distally-directed force on any suitable portion of pusher 306 and maintaining the position of the housing 302, advancing the housing 302 in a proximal direction (e.g., by applying a proximally-directed force on any suitable portion of the housing 302) while maintaining the position of pusher 306, or advancing pusher 306 in a distal direction relative to the housing 302. FIG. 6B illustrates catheter 420 passed through cannula lumen 332 such that the portion of the elongate member 422 that defines the elongate member curve 440 is free of, or outside of, the cannula lumen 332 and the elongate member 422 has moved from the first configuration to the second curved configuration. This step is considered advantageous at least because the structural arrangement of the elongate member 422 (e.g., curved relative to the cannula 304) provides a mechanism for locating and treating the maxillary sinus ostium 354 without requiring the guidance of a previously placed guide wire. Thus, any of the steps described herein can be accomplished without a previously placed guide wire.

Step 508 can be accomplished by advancing the delivery device, or the elongate member distal end 428 toward the sinus passage wall 355 (e.g., by applying a force along an axis that passes through elongate member first axis 442 at an angle on any suitable portion of the delivery device). An optional step comprises applying torque to any suitable portion the delivery device 300 (e.g., housing 302, cannula 304, pusher 306) to cause the elongate member distal end 428 to rotate relative to the cannula 304 and/or bodily passage. Tactile feedback will be provided to the user of the delivery device 300 once the maxillary sinus ostium 354 has been located (e.g., the elongate member distal end 428 will enter, or pass through, the maxillary sinus ostium 354). These steps are considered advantageous at least because they provide a mechanism for locating the maxillary sinus ostium 354 without a visualization device. Alternatively, step 508 can be accomplished using direct visualization of the elongate member (e.g., scope), transcutaneously, transillumination techniques, using a camera, or any other suitable visualization technique independent of, or in combination with, tactile feedback.

Step 510 can be accomplished by continuing the application of distally-directed force on any suitable portion of the pusher 306 and maintaining the position of the housing 302, advancing housing 302 in a proximal direction (e.g., by applying a proximally-directed force on any suitable portion of the housing 302) while maintaining the position of pusher 306, or advancing pusher 306 in a distal direction relative to the housing 302, until the catheter 420 passes through the maxillary sinus ostium 356. This step can be accomplished with the assistance of direct visualization of the cannula (e.g., scope), transcutaneously, transillumination techniques, using a camera, or any other suitable visualization technique.

Figure 6C:
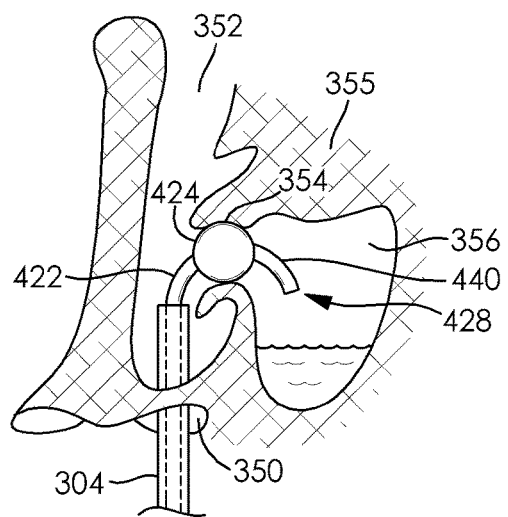
FIG. 6C is a partial sectional view of a patient with the delivery device illustrated in FIG. 5 partially disposed in a nasal passage. The balloon of the catheter is in the inflated configuration.

The length of the catheter 420 passed through the maxillary sinus ostium 354 will depend on the procedure intended to be completed. In the illustrated embodiment, as shown in FIG. 6C, the elongate member distal end 428 is passed through the maxillary sinus ostium 354 such that the balloon 424 is positioned within the maxillary sinus ostium 354 and the elongate member distal end 428 is disposed within the maxillary sinus cavity 356. The positioning of the balloon 424 in this manner is considered advantageous at least because it provides a mechanism for dilating the maxillary sinus ostium 354 such that subsequent to dilation fluid can flow from the maxillary sinus cavity 356.

Alternatively, the elongate member distal end 428 can be passed into the maxillary sinus cavity 356 such that the balloon 424 is positioned within the maxillary sinus cavity 356. The balloon 424 can optionally be disposed entirely, or partially, within the maxillary sinus cavity 356. The positioning of the balloon 424 in this manner is considered advantageous at least because it provides a mechanism for dilating the maxillary sinus cavity 356.

An optional step comprises confirming placement of the balloon 420 at a desired point of treatment. This step can be accomplished using any suitable visualization device or technique. For example, this optional step can be accomplished with the assistance of direct visualization of the elongate member (e.g., scope), transcutaneously, using transillumination techniques (e.g., catheter includes a optical fiber attached to a light source), using a camera, or any other suitable visualization technique.

Step 512 can be accomplished by passing a fluid through the pusher lumen 344 and the inflation lumen 438 and into the balloon chamber 460 to move the balloon 424 from its first deflated configuration toward its second inflated configuration, or to the second configuration. For example, a syringe in communication with the pusher lumen 344 and the inflation lumen 438 can be used to introduce the fluid into the balloon chamber 460. The amount of the exterior surface of the balloon 424 that contacts the tissue in the maxillary sinus ostium 354, and the amount of pressure exerted by the exterior surface of the balloon 424 onto the tissue in the maxillary sinus ostium 354, will depend on the amount of fluid introduced into the balloon chamber 460. FIG. 6C illustrates catheter 420 passed through the maxillary sinus ostium 354 and the balloon 424 in the inflated configuration. Examples of fluids considered suitable to pass through an inflation lumen 438 and into a balloon chamber 460 are described above.

Step 514 can be accomplished by stopping the step of passing fluid through the pusher lumen 344 and inflation lumen 438 and into the balloon chamber 460. This can be accomplished, for example, by stopping the application of the distally-directed force on the plunger of the syringe.

Step 516 can be accomplished by removing the fluid, or a portion of the fluid, passed into the balloon chamber 460. For example, a syringe in communication with the pusher lumen 344 and the inflation lumen 438 can be used to provide vacuum pressure to remove the fluid, or a portion of the fluid, from the balloon chamber 460. The amount of fluid removed from the balloon chamber 460 can vary depending on the procedure. For example alternative to removing a portion of the fluid, all of the fluid, or substantially all of the fluid, can be removed from the balloon chamber 460.

Optionally step 512, step 514, and 516 can be repeated.

Step 518 can be accomplished by applying a proximally-directed force on any suitable portion of pusher 306 and maintaining the position of the housing 302, advancing housing 302 in a distal direction (e.g., by applying a distally-directed force on any suitable portion of the housing 302) while maintaining the position of pusher 306 relative to the housing 302, or advancing pusher 306 in a proximal direction relative to the housing 302.

Figure 6D:
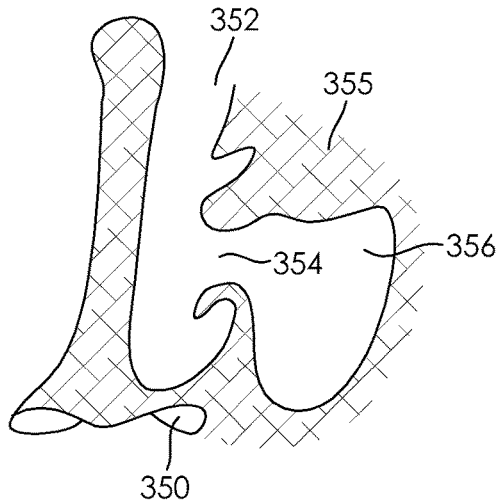
FIG. 6D is a partial sectional view of a nasal passage following treatment.

Step 520 can be accomplished by applying a proximally-directed force on any suitable portion of the delivery device 300 (e.g., housing 302) such that the delivery device 300 is withdrawn from the nasal passage 352. FIG. 6D illustrates the maxillary sinus ostium 354 subsequent to dilation and the removal of the catheter 420 from the maxillary sinus ostium 354 and the delivery device 300 from the nasal passage 352. In FIG. 6D, the maxillary sinus ostium 354 is unblocked allowing material within the maxillary sinus cavity 356 to drain and air to circulate throughout the maxillary sinus cavity 356.

While step 518 and step 520 have been described as separate steps, step 518 and step 520 can be accomplished concurrently with one another.

While method 500 has been described and illustrated as a method of treating a maxillary sinus ostium 354 defined by a sinus passage wall 355, the delivery devices, catheters, and/or cannulas described herein can be used to treat any suitable opening and/or the tissue of any suitable bodily passage, sinus passage, airway, and/or sinus cavity. Skilled artisans will be able to select a suitable opening and/or tissue to treat according to a particular embodiment based on various considerations, including the treatment desired to be performed.

It is considered advantageous to complete method 500 in the order illustrated and/or described. It is noted, however, that any order is considered suitable.

While various steps, alternative steps, and optional steps have been described above with respect to treating a maxillary sinus ostium defined by a sinus passage wall, these steps, alternative steps, and optional steps can be included in, accomplished concurrently with, and/or accomplished in the alternative to, the methods, steps, alternative steps, and/or optional steps described above and/or below with respect to treating tissue in a wall defining a bodily passage.

FIGS. 7, 8, and 9 illustrate another exemplary cannula 600, catheter 620, and insert 700 for accomplishing any suitable method and/or step, such as those described herein. The cannula 600 is similar to the cannula 200 illustrated in FIGS. 2 and 3 and described above, except as detailed below. The balloon catheter 620 is similar to the balloon catheter 220 illustrated in FIGS. 2 and 3 and described above, except as detailed below. Reference numbers in FIGS. 7, 8, and 9 refer to the same structural element or feature referenced by the same number in FIGS. 2 and 3, offset by 400.

In the illustrated embodiment, the elongate member body 630 defines an inflation port 631, a device port 633, an elongate member first opening 634, an elongate member second opening 636, an elongate member third opening 635, an elongate member fourth opening 637, an inflation lumen 638, a device lumen 639, and an elongate member curve 640.

The elongate member first opening 634 is disposed on the inflation port 631 and the elongate member second opening 636 is disposed between the elongate member proximal end 626 and the elongate member distal end 628. The inflation lumen 638 extends from the elongate member first opening 634 to the elongate member second opening 636. The elongate member third opening 635 is disposed on the elongate member proximal end 626 and the elongate member fourth opening 637 is disposed on the elongate member distal end 628. The device lumen 639 extends from the elongate member third opening 635 to the elongate member fourth opening 637. The elongate member body 630 defines the elongate member curve 640 between the elongate member proximal end 626 and the elongate member distal end 628. In the illustrated embodiment, the elongate member curve 640 is defined between the balloon 624 and the elongate member distal end 628. Optionally, the elongate member 622 can omit the inclusion of an elongate member curve 640 (e.g., predefined curve) and a curve can be defined independently by an insert, such as insert 700, as described below.

The inflation port 631 and/or device port 633 can include any suitable connector and/or adapter capable of attaching, or assisting with attaching, one or more devices to the elongate member 622. Skilled artisans will be able to select a suitable connector and/or adapter to include on an elongate member according to a particular embodiment based on various considerations, including the materials that form the elongate member. Example connectors and/or adapters considered suitable to include on an elongate member include, but are not limited to, threaded connectors, Tuohy Borst adapters, luer lock connectors, and any other connector and/or adapter considered suitable for a particular application.

In the illustrated embodiment, the balloon 624 is attached to elongate member 622 between the elongate member proximal end 626 and the elongate member distal end 628 at the balloon proximal junction 650 and the balloon distal junction 652. The balloon 624 comprises a balloon proximal end 654, a balloon distal end 656, and a balloon wall 658. The balloon wall 658 and the portion of the surface of the elongate member 622 disposed within the balloon 624 define the balloon chamber 660 that is adapted to receive a fluid such that the balloon 624 can be moved between a first deflated configuration and a second inflated configuration. FIG. 7 illustrates the balloon 624 in the first deflated configuration and FIG. 8 illustrates balloon 624 in the second inflated configuration.

The balloon 624 is attached to the elongate member 622 such that the elongate member second opening 636 is in communication with the balloon chamber 660. With this structural arrangement, the balloon 624 is adapted to move between the first deflated configuration and second inflated configuration as fluid is moved into and out of the balloon chamber 660 via the inflation lumen 638 and the elongate member second opening 636.

In the illustrated embodiment, the insert 700 is disposed within the device lumen 639, as shown in FIGS. 7 and 8. For clarity, the insert 700 is shown in FIG. 9 free of the device lumen 639. The insert 700 comprises an insert proximal end 702, an insert distal end 704, and an insert body 706. The insert 700 has an insert length that extends from the insert proximal end 702 to the insert distal end 704. The insert body 706 defines a proximal portion 708, a distal portion 710, and an insert curve 712.

The insert 700 has an insert length than is greater than the length of the catheter 720, a first outside diameter 709 along the proximal portion 708, and a second outside diameter 711 along the distal portion 710. However, the length of a insert can alternatively be less than, equal to, or substantially equal to, the length of a catheter. The first outside diameter 709 is greater than the second outside diameter 711 and greater than the inside diameter of the device lumen 639. The second outside diameter 711 is less than the inside diameter of device lumen 639. The insert proximal portion 708 acts as a mechanical stop to distal advancement of the insert proximal portion 708 beyond the elongate member proximal end 626. Optionally, insert first portion can be omitted and an insert can have a continuous, or substantially continuous, outside diameter along its length.

The insert 700 is adapted to move between a first straight, or substantially straight, configuration and a second curved configuration. In the first straight, or substantially straight, configuration, the portion of the insert 700 that defines the insert curve 712 is straight, or substantially straight, when the elongate member 622 is disposed within the cannula lumen 612, as illustrated in FIG. 7. In the second curved configuration, the portion of the insert 700 that defines the insert curve 712 is curved when the elongate member 622 is free of, or disposed outside of, the cannula lumen 612, as illustrated in FIG. 8. Thus, the insert 700 is biased to the second curved configuration (e.g., the insert 700 has a predefined curve).

The insert 700 has an insert first axis 714 and an insert second axis 716 disposed at an angle to the insert first axis 714. The insert first axis 714 extends through a portion, or the entirety, of the insert body 706 disposed proximal to the insert curve 712. The insert second axis 716 extends through the insert first axis 714 and through the insert distal end 704 (e.g., center of insert distal end 704) when the insert 700 is free of the elongate member 622 and in the second curved configuration.

In the illustrated embodiment, the insert second axis 716 is disposed at a first angle 717 relative to the insert first axis. The first angle 717 is equal to, or substantially equal to, 45 degrees. Alternative angles that are considered suitable are illustrated in hidden lines in FIG. 9. For example, an insert curve 712 can be disposed such that an insert second axis 716' is disposed at a second angle 717' relative to an insert first axis, or such that an insert second axis 716" is disposed at a third angle 717" relative to an insert first axis. The second angle 717' is equal to, or substantially equal to, 90 degrees. The third angle 717" is equal to, or substantially equal to, 135 degrees.

While particular angles have been described with respect to the insert curve 712, an insert can define any suitable angle between an insert first axis and an insert second axis. Skilled artisans will be able to select a suitable angle to define between an insert first axis and an insert second axis according to a particular embodiment based on various considerations, including the procedure intended to be performed. Example angles considered suitable to define between an insert first axis and an insert second axis include, but are not limited to, acute angles, obtuse angles, a 45 degree angle, a substantially 45 degree angle, an angle about 45 degrees, a 90 degree angle, a substantially 90 degree angle, an angle about 90 degrees, a 135 degree angle, a substantially 135 degree angle, an angle about 135 degrees, and any other angle considered suitable for a particular application.

The insert curve 712 can be formed in the insert 700 using any suitable technique, and skilled artisans will be able to select a suitable technique to form a curve in an insert according to a particular embodiment based on various considerations, including the material forming an insert. An example technique considered suitable to form a curve in an insert includes, but is not limited to, positioning the insert in the second curved configuration and then applying heat to the portion of the insert in which it is desired to form a curve such that the curve is incorporated into the material that forms the insert.

The insert 700 can be formed of any suitable material and fabricated using any suitable technique, and skilled artisans will be able to select a suitable material to form an insert and a suitable technique to fabricate an insert according to a particular embodiment based on various considerations, including the material that forms an elongate member intended to be used with an insert. Example materials considered suitable to form an insert include, but are not limited to, biocompatible materials, materials that can be made biocompatible, metals such as stainless steel, titanium, nitinol, cobalt chromium, polymers, Pebax (Pebax is a registered trademark of Ato Chimie Corporation of Allee des Vosges, Courbevoie, France), nylon, polyethylene, polyurethane, silicone, coiled materials, braided materials, and any other material considered suitable for a particular application. Optionally, an insert can be formed of a malleable material such that the angle defined between an insert first axis and an insert second axis can be formed prior to the performed of a procedure and/or adjusted as needed.

In use, the insert 700 is advanced through the device lumen 639 such that the insert proximal portion 708 contacts the elongate member proximal end 626 and the insert curve 712 is disposed within the device lumen 639. The insert 700 is adapted to move the elongate member 622 between the first straight configuration and the second curved configuration, as shown in FIGS. 7 and 8, and as described herein. Alternatively, if the insert 700 omits the inclusion of the insert proximal end 708, the insert 700 can be advanced through the device lumen 639 until the insert curve 712 is disposed entirety within, or partially within, the device lumen 639.

Optionally, an optical fiber can be attached to the insert 700 or disposed within, or attached within, the device lumen 639 such that a treatment site can be illuminated prior to, during, or subsequent to treatment being performed. Any suitable optical fiber can be used and operatively connected to any suitable light source.

FIG. 10 illustrates an exemplary kit 780 comprising a cannula 800 according to an embodiment, such as cannula 600 illustrated in FIG. 7; a balloon catheter 820 according to an embodiment, such as balloon catheter 620 illustrated in FIGS. 7 and 8; a first insert 900 according to an embodiment, such as insert 700 illustrated in FIGS. 7, 8, and 9; a second insert 920; a third insert 940; and instructions for use 960.

The first insert 900 defines a first angle between the insert first axis and the insert second axis. The second insert 920 defines a second angle between the insert first axis and the insert second axis. The third insert 940 defines a third angle between the insert first axis and the insert second axis. The first angle is different than the second angle and the second angle is different than the third angle. Alternatively, a kit can include one or more inserts or two or more inserts, each having different angles defined between an insert first axis and an insert second axis, or at least two inserts having different angles defined between an insert first axis and an insert second axis.

While kit 780 has been described as including a first insert 900, a second insert 920, and a third insert 940, a kit can include any suitable number of inserts, each defining any suitable angle between an insert first axis and an insert second axis. Skilled artisans will be able to select a suitable number of inserts to include in a kit according to a particular embodiment based on various considerations, including the type of procedure intended to be performed with the devices included in a kit. Example number of inserts considered suitable to include in a kit include, but are not limited to, one, at least one, two, a plurality, three, four, and any other number considered suitable for a particular application. Each of the inserts can have a different angle defined between an insert first axis and an insert second axis, or two or more inserts can have the same angle defined between an insert first axis and an insert second axis. Optionally, a deflectable insert, such that insert 1100, can be included in any suitable kit, such as kit 780, or any other kit described herein.

Figure 11:
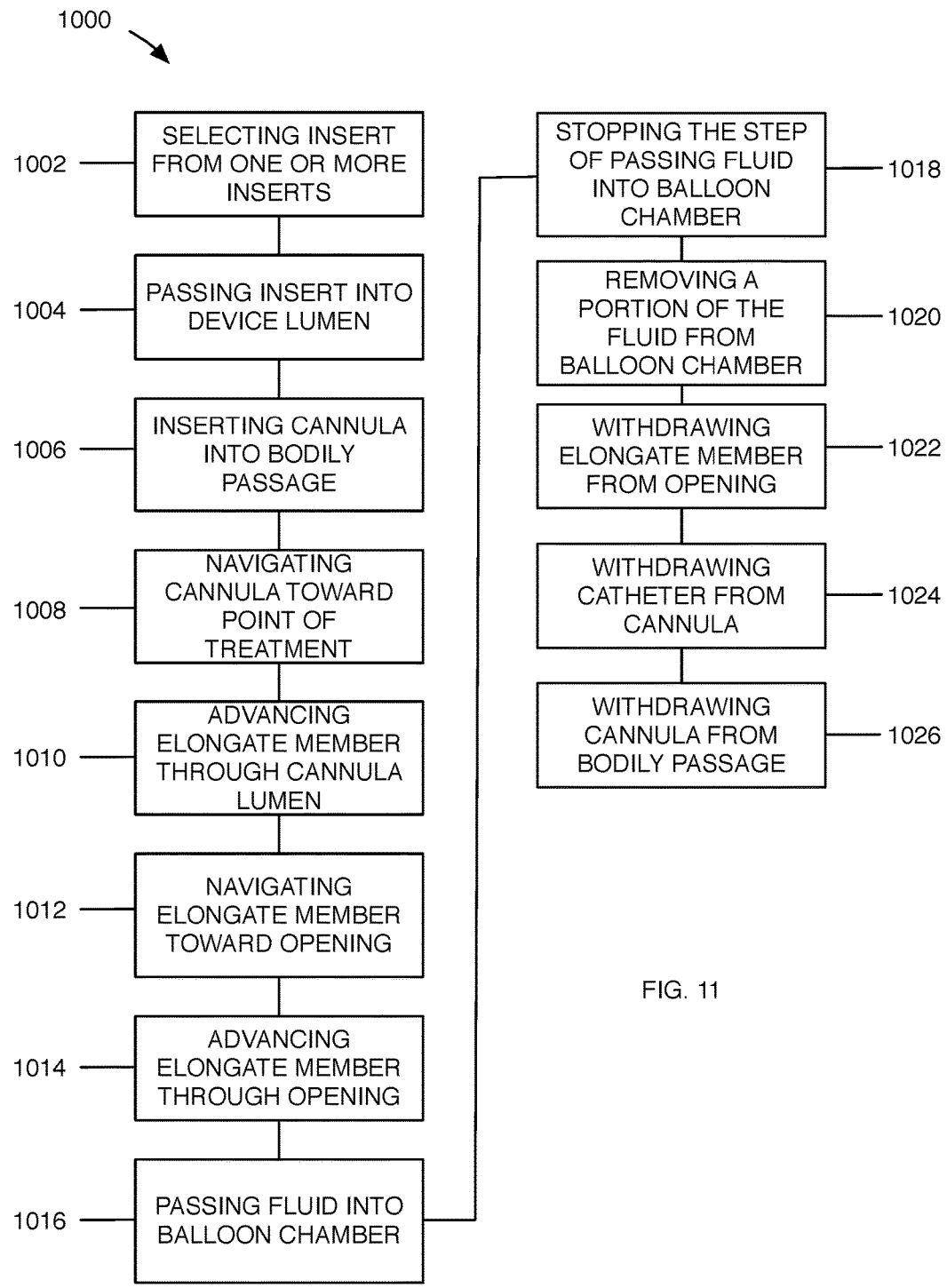
FIG. 11 is a flowchart representation of another exemplary method of treating tissue in a wall defining a bodily passage.

FIG. 11 is a flowchart representation of an exemplary method 1000 of treating tissue in a passage wall defining a bodily passage.

A step 1002 comprises selecting an insert from one or more inserts. The insert has an insert proximal end, an insert distal end, an insert length, and an insert body that defines an insert curve. The insert length extends from the insert proximal end to the insert distal end. The insert curve is defined along a portion of the insert. The insert is adapted to move between a first straight, or substantially straight, configuration in which the portion of the insert that defines the insert curve is straight, or substantially straight, when an elongate member is disposed within the cannula lumen and a second curved configuration in which the portion of insert that defines the insert curve is curved when the elongate member is free of, or disposed outside of, the cannula lumen. Another step 1004 comprises passing the insert into a device lumen defined by a catheter. The catheter disposed within a cannula having a cannula proximal end, a cannula distal end, and a cannula body defining a cannula lumen. The catheter having an elongate member and balloon. The elongate member having an elongate member proximal end, an elongate member distal end, an elongate member length, and an elongate member body that defines an inflation lumen, a device lumen, and an elongate member curve. The elongate member length extends from the elongate member proximal end to the elongate member distal end. The elongate member curve is defined along a portion of the elongate member. The elongate member is adapted to move between a first straight, or substantially straight, configuration in which the portion of the elongate member that defines the elongate member curve is straight, or substantially straight, when disposed within the cannula lumen and a second curved configuration in which the portion of elongate member that defines the elongate member curve is curved when free of, or disposed outside of, the cannula lumen. The balloon is disposed on the elongate member and has a balloon wall that defines a balloon chamber in communication with the inflation lumen. The balloon is moveable between a first deflated configuration and a second inflated configuration as fluid is moved into and out of the balloon chamber. Another step 1006 comprises inserting the cannula into a bodily passage such that the cannula distal end is disposed within the bodily passage. Another step 1008 comprises navigating the cannula toward a point of treatment within the bodily passage. The point of treatment comprises an opening defined by the wall of the bodily passage. Another step 1010 comprises advancing the elongate member distally through the cannula lumen such that the portion of the elongate member that defines the elongate member curve is free of, or disposed outside of, the cannula lumen and the elongate member moves from the first configuration to the second configuration. Thus, the elongate member adopts a curved configuration. Another step 1012 comprises navigating the elongate member distal end toward the opening defined by the passage wall. Another step 1014 comprises advancing the elongate member distal end through the opening defined by the passage wall such that the balloon is positioned through the opening. Another step 1016 comprises passing a fluid through the inflation lumen and into the balloon chamber to move the balloon toward the second inflated configuration. Another step 1018 comprises stopping the step of passing a fluid through the inflation lumen and into the balloon chamber. Another step 1020 comprises removing a portion of the fluid from the balloon chamber. Another step 1022 comprises withdrawing the elongate member from the opening defined by the passage wall. Another step 1024 comprises withdrawing the catheter from the cannula lumen. Another step 1026 comprises withdrawing the cannula from the bodily passage.

Step 1002 can be accomplished by selecting any suitable insert according to an embodiment, such as the embodiments described and illustrated herein. Skilled artisans will be able to second a suitable insert according to a particular embodiment based on various considerations, including the treatment intended to be performed. Examples of inserts considered suitable include, but are not limited to, insert 700, insert 900, insert 920, insert 940, insert 1100, and any other insert described herein and/or considered suitable for a particular application.

Step 1004 can be accomplished using any suitable cannula and/or catheter according to an embodiment, such as the embodiments described and illustrated herein. Skilled artisans will be able to select a suitable cannula and/or catheter according to a particular embodiment based on various considerations, including the treatment intended to be performed. Examples of cannulas considered suitable include, but are not limited to, cannula 200, cannula 600, and any other cannula described herein and/or considered suitable for a particular application. Examples of catheters considered suitable include, but are not limited to, catheter 220, catheter 620, and any other catheter described herein and/or considered suitable for a particular application.

Step 1004 can be accomplished by introducing the insert distal end into the proximal opening of a device lumen of a catheter and applying a distally-directed force on the insert until the proximal portion of the insert contacts the proximal end of the elongate member, or until the insert curve is entirety, or partially, disposed within the device lumen of the elongate member. Alternatively, in embodiments in which the insert omits the inclusion of a proximal portion, the distally-directed force can be applied to the insert until the insert curve is disposed within the device lumen of the elongate member.

Alternatively, an insert can be pre-loaded within an elongate member such that steps 1002 and 1004 can be omitted from method 1000. An insert can be pre-loaded and/or inserted into any suitable catheter, such as those described herein. For example, any of the catheters described herein can include a lumen that extends from an opening on the proximal end of the catheter toward the distal end of the catheter (e.g., an opening on the distal end of the catheter) and any of the inserts described herein can be advanced into, or positioned within, the lumen defined by the catheter.

Step 1006 can be accomplished as described above with respect to step 102. Step 1008 can be accomplished as described above with respect to step 106. Step 1010 can be accomplished as described above with respect to step 108. Step 1012 can be accomplished as described above with respect to step 110. Step 1014 can be accomplished as described above with respect to step 112. Step 1016 can be accomplished as described above with respect to step 114. Step 1018 can be accomplished as described above with respect to step 116. Step 1020 can be accomplished as described above with respect to step 118. Step 1022 can be accomplished as described above with respect to step 120. Step 1024 can be accomplished as described above with respect to step 122. Step 1026 can be accomplished as described above with respect to step 124. When an insert is disposed within an elongate member, as described herein, any of the steps described herein that include applying a force to a catheter and/or elongate member can optionally include simultaneously, or separately, applying a force in the same direction as the force applied to the catheter and/or elongate member on an insert.

It is considered advantageous to complete method 1000 in the order illustrated and/or described. It is noted, however, that any order is considered suitable.

While various steps, alternative steps, and optional steps have been described above with respect to treating tissue in a passage wall defining a bodily passage, these steps, alternative steps, and optional steps can be included in, accomplished concurrently with, and/or accomplished in the alternative to, the methods, steps, alternative steps, and/or optional steps described above and/or below with respect to treating tissue in a passage wall defining a bodily passage and/or treating tissue in a passage wall defining a sinus passage.

Figure 12:
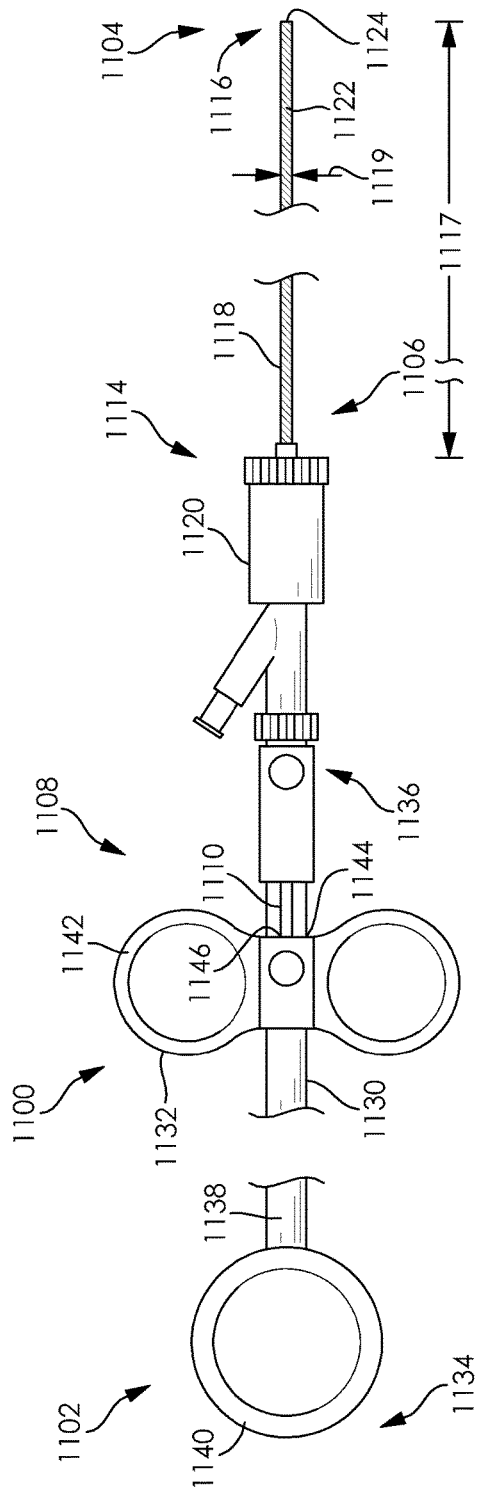
FIG. 12 is a side view of another exemplary insert. The insert is in the first straight, or substantially straight, configuration.
Figure 13:
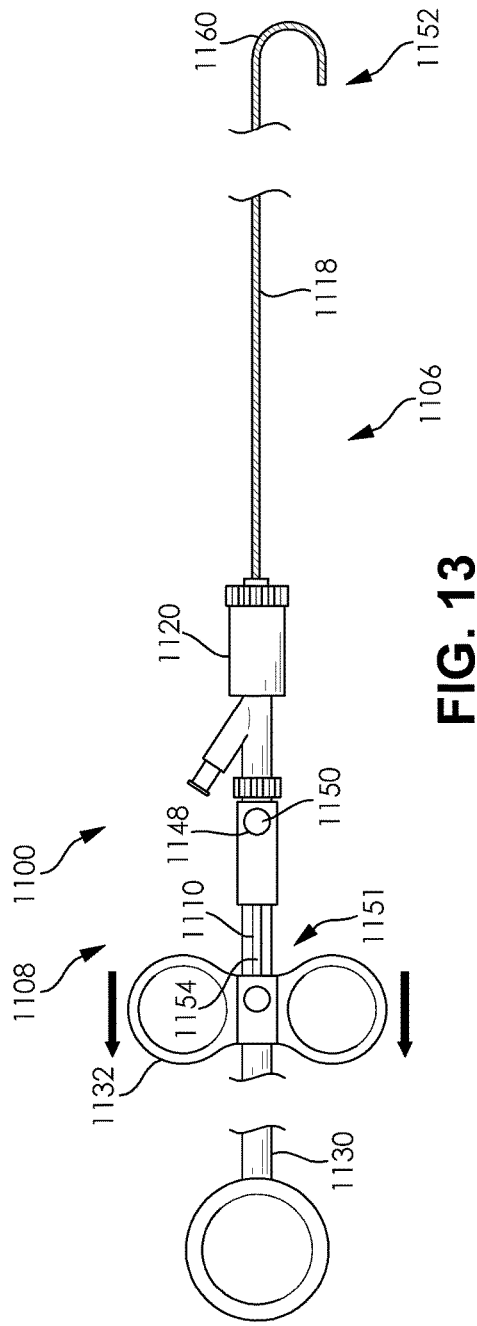
FIG. 13 is a side view of the exemplary insert illustrated in FIG. 12 in the second curved configuration.

FIGS. 12 and 13 illustrate another exemplary insert 1100 that can be used with any of the devices described herein and to complete any suitable method and/or step, such as those described herein. Insert 1100 is described as being used in combination cannula 600 and balloon catheter 620. For example, the insert 1100 can be disposed within the device lumen 639, as shown in FIGS. 7 and 8, alternative to the insert 700 illustrated in FIGS. 7 and 8, such that the distal end of the insert 1100 is disposed proximal to the distal end 628 of the balloon catheter 620. However, the insert 1100 can be used with any suitable device.

In the illustrated embodiment, the insert 1100 comprises a proximal end 1102, a distal end 1104, a deflectable member 1106, a handle 1108, and a tension member 1110. The deflectable member 1102 is configured to move between a first straight, or substantially straight, configuration, as shown in FIG. 12, and a second curved configuration, as shown in FIG. 13. This provides a mechanism to move the device within which the insert 1100 is disposed (e.g., catheter 620) between a first straight, or substantially straight, configuration and a second curved configuration during use.

While a particular structural configuration has been illustrated for the insert 1100, any suitable insert capable of moving between a straight, or substantially straight, configuration and a curved configuration can used with the devices described herein and/or to accomplish any of the methods and/or steps described herein. Skilled artisans will be able to select a suitable insert to use in combination with the devices described herein and/or to accomplished any of the methods and/or steps described herein according to a particular embodiment based on various considerations, such as the structural arrangement of a catheter intended to be used with the insert and/or the structural arrangement at a point of treatment. An example insert considered suitable to use in combination with the devices described herein and/or to complete one or more of the methods and/or steps described herein includes the Reuter Tip Deflecting Wire Guide Handle and Wire Guide provided by Cook Medical and described in manual T-TDWIRE-REVO, published in February of 2012. The contents of this manual are hereby incorporated into this disclosure in its entirety. However, other inserts that include a deflectable member can be used in combination with the devices described herein and/or to complete one or more of the methods and/or steps described herein.

The deflectable member 1106 a proximal end 1114, a distal end 1116, a shaft 1118, and a connector 1120. The shaft 1118 has a length 1117, an outside diameter 1119, and a body 1122 that defines a lumen 1124. The length 1117 of the shaft 1118 is greater than the length of the catheter 620. However, the shaft of a deflectable member can have any suitable length, such as a length that is less than, equal to, or substantially equal to, the length of a device through which it is disposed. The outside diameter 1119 is less than the inside diameter of the device lumen 639 of the catheter 620. The lumen 1124 extends from an opening on the proximal end 1114 to an opening on the distal end 1116 of the deflectable member 1106. However, alternative embodiments can include a deflectable member that defines a lumen that extends from an opening on the proximal end to a location between the proximal end and the distal end such that the distal end is sealed, or capped.

The shaft 1118 of a deflectable member 1106 can be formed of any suitable material and fabricated using any suitable technique, and skilled artisans will be able to select a suitable material to form a shaft of a deflectable member and a suitable technique to fabricate a shaft of a deflectable member according to a particular embodiment based on various considerations, including the desired flexibility of the shaft. Example materials considered suitable to form a shaft include, but are not limited to, biocompatible materials, materials that can be made biocompatible, metals such as stainless steel, titanium, nitinol, cobalt chromium, polymers, Pebax (Pebax is a registered trademark of Ato Chimie Corporation of Allee des Vosges, Courbevoie, France), nylon, polyethylene, polyurethane, silicone, coiled materials, braided materials, and any other material considered suitable for a particular application. For example, a first portion of a shaft can be formed as a solid tubular member and a second portion of a shaft can be formed of a coiled material to impart flexibility into the shaft.

The connector 1120 acts as a mechanical stop to distal advancement of the insert 1100 beyond the elongate member proximal end 626. The connector 1120 can comprise any suitable structure capable of attaching, or assisting with attaching, the handle 1108 to the deflectable member 1106 and that defines a passageway through which the tension member 1110 can be disposed. Skilled artisans will be able to select a suitable connector to include on an insert according to a particular embodiment based on various considerations, including the materials that form the deflectable member included on an insert on which the connector is a component. Example structures considered suitable to include on a connector include, but are not limited to, threaded connectors, Tuohy Borst adapters, luer lock connectors, friction fit configurations, snap fit configurations, and any other structure considered suitable for a particular application.

The handle 1108 comprises an elongate member 1130 and an actuator 1132 slidably disposed on the elongate member 1130. The elongate member 1130 has a proximal end 1134, a distal end 1136, and a body 1138 that defines a thumb ring 1140. The proximal end 1134 of the elongate member 1130 includes a corresponding structure capable of attaching the handle 1108 to the connector 1120, such as those described above with respect to the connector 1120.

The actuator 1132 is disposed between the proximal end 1134 and the distal end 1136 of the elongate member 1130 and comprises a body 1142 that defines a first passageway 1144, a second passageway 1146, and a third passageway 1148. In addition, the actuator 1132 includes a lock screw 1150 disposed within the third passageway 1148. The first passageway 1144 is sized and configured to receive a portion of the elongate member 1130. The second passageway 1146 is sized and configured to receive a portion of the tension member 1110. The third passageway 1148 is sized and configured to receive a portion of the lock screw 1150 and is in communication with the second passageway 1146. The actuator 1132 is slidably disposed on the elongate member 1130 such that the elongate member 1130 is positioned through the first passageway 1142. The lock screw 1150 provides a mechanism for releasably attaching a portion of the tension member 1110 to the actuator 1132, as described in more detail herein. While a lock screw 1150 has been illustrated as providing a mechanism to releasably attach the tension member 1110 to the actuator 1132, any suitable technique or method of attachment can be used to releasably or fixedly attach a tension member to an actuator.

The actuator 1132 is movable between a first position and a second position. In the first position, the actuator 1132 is disposed a first distance from the distal end 1136 of the elongate member 1130 and in the second position the actuator 1132 is disposed a second distance from the distal end 1136 of the elongate member 1130 that is greater than the first distance. The deflectable member 1106 is in the first straight, or substantially straight, configuration when the actuator 1132 is in the first position and the deflectable member 1106 is in the second curved configuration when the actuator 1132 is in the second position.

While a an actuator 1132 that is slidably disposed on an elongate member 1130 has been illustrated, an insert can include any suitable actuator capable of moving a deflectable member between a first straight, or substantially straight, configuration and a second curved configuration. Skilled artisans will be able to select a suitable actuator to include on an insert according to a particular embodiment based on various considerations, including the structural arrangement of the insert. Example actuators considered suitable to include on an insert include depressible members, rotatable members, slidable members, linear actuators, pivotable actuators, levers, and any other actuator considered suitable for a particular embodiment.

The tension member 1110 comprises a proximal end 1151, a distal end 1152, and a body 1154. The proximal end 1151 of the tension member 1110 is disposed within the second passageway 1146 defined by the actuator 1132 and is releasably attached to the actuator 1132 using lock screw 1150. The distal end 1152 of the tension member 1110 is attached within the lumen 1124 defined by the deflectable member 1106 (e.g., at the distal end, proximal to the distal end). The tension member 1110 extends from the proximal end 1151, through the connector 1120, and through the lumen 1124 defined by the deflectable member 1106, to the distal end 1152.

The connector 1120, elongate member 1130, actuator 1132, and tension member 1110 can be formed of any suitable material and fabricated using any suitable technique. Skilled artisans will be able to select a suitable material to form a connector, elongate member, actuator, and/or tension member of an insert and a suitable technique to fabricate a connector, elongate member, actuator, and/or tension member of an insert according to a particular embodiment based on various considerations, including the material(s) that form a deflectable member. Example materials considered suitable to form a connector, elongate member, actuator, and/or tension member include, but are not limited to, biocompatible materials, materials that can be made biocompatible, metals such as stainless steel, titanium, nitinol, cobalt chromium, polymers, Pebax (Pebax is a registered trademark of Ato Chimie Corporation of Allee des Vosges, Courbevoie, France), nylon, polyethylene, polyurethane, silicone, coiled materials, braided materials, and any other material considered suitable for a particular application.

The insert 1100 is adapted to move between a first straight, or substantially straight, configuration and a second curved configuration. In the first straight, or substantially straight, configuration, the actuator 1132 is in the first position and deflectable member 1106 is straight, or substantially straight. In the second curved configuration, the actuator 1132 is in the second position and the and deflectable member 1106 defines an insert curve 1160 between the proximal end 1114 and the distal end 1116 of the deflectable member 1106. Therefore, when the insert 1100 is disposed within the lumen of another device the portion of the insert 1100 that defines the insert curve 1160 is curved and forms a curve in the device through which the insert is disposed. For example, when the insert 1100 is disposed within the device lumen 639 of catheter 620, the portion of the insert 1100 that defines the insert curve 1160 is curved and forms a curve in the catheter 620 along its length. The catheter 620 is straight, or substantially straight, when the insert 1100 is in the first configuration (e.g., actuator 1132 is in the first position) and the catheter 620 is curved when the insert 1100 is in the second configuration (e.g., actuator 1132 is in the second position). The catheter 620, therefore, is adapted to adopt the configuration of the insert 1100 (e.g., deflectable member 1106).

An insert can define any suitable angle between a first axis disposed along a first portion of the insert that is disposed proximal to the insert curve and a second axis disposed along a second portion of the insert disposed distal to the insert curve. Skilled artisans will be able to select a suitable angle to define between a first axis and a second axis according to a particular embodiment based on various considerations, including the procedure intended to be performed. Example angles considered suitable to define between a first axis and a second axis include, but are not limited to, acute angles, obtuse angles, a 45 degree angle, a substantially 45 degree angle, an angle about 45 degrees, a 90 degree angle, a substantially 90 degree angle, an angle about 90 degrees, a 135 degree angle, a substantially 135 degree angle, an angle about 135 degrees, and any other angle considered suitable for a particular application.

In use, the insert 1100 is advanced through the device lumen 639 such that the distal end 1116 of the deflectable member 1106 is disposed proximal to the distal end 628 of the catheter 620 and/or such that the connector 1120 contacts the elongate member proximal end 626. The insert 1100 is adapted to move the elongate member 622 between the first straight configuration and the second curved configuration.

Optionally, an optical fiber can be attached to the insert 1100 or disposed within, or attached within, the device lumen 639 such that a treatment site can be illuminated prior to, during, or subsequent to treatment being performed. Any suitable optical fiber can be used and operatively connected to any suitable light source.

Figure 14:
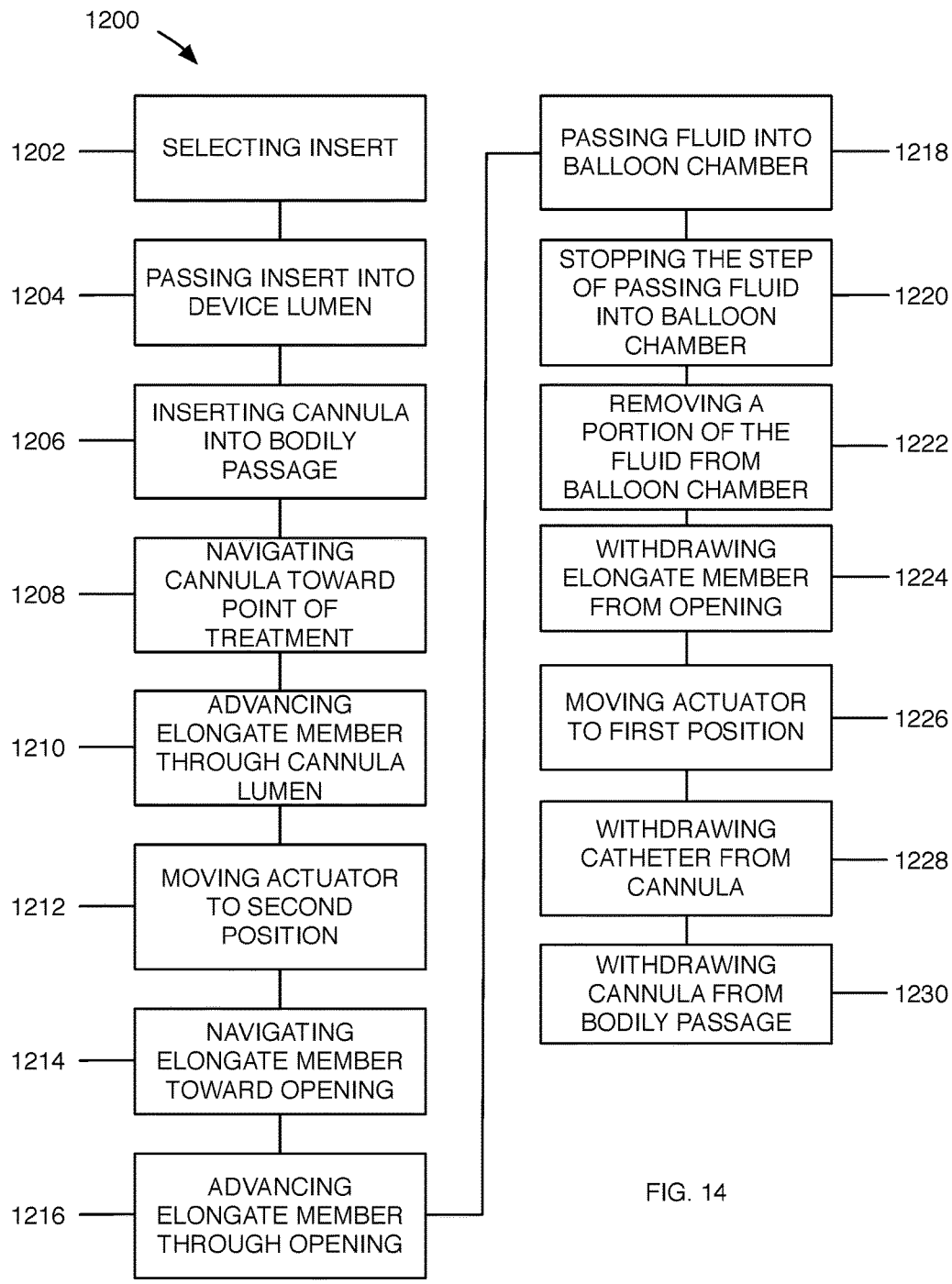
FIG. 14 is a flowchart representation of another exemplary method of treating tissue in a wall defining a bodily passage.

FIG. 14 is a flowchart representation of an exemplary method 1200 of treating tissue in a passage wall defining a bodily passage.

A step 1202 comprises selecting an insert. The insert has an insert proximal end, an insert distal end, and is adapted to define an insert curve. The insert is adapted to move between a first straight, or substantially straight, configuration and a second curved configuration in which the insert defines the insert curve. Another step 1204 comprises passing the insert into a device lumen defined by a catheter. The catheter disposed within a cannula having a cannula proximal end, a cannula distal end, and a cannula body defining a cannula lumen. The catheter having an elongate member and balloon. The elongate member having an elongate member proximal end, an elongate member distal end, an elongate member length, and an elongate member body that defines an inflation lumen, and a device lumen. The elongate member length extends from the elongate member proximal end to the elongate member distal end. The elongate member is adapted to define an elongate member curve when the insert is in the second configuration (e.g., actuator 1132 is in the second position). The elongate member is adapted to move between a first straight, or substantially straight, configuration and a second curved configuration in which the elongate member defines the elongate member curve. The elongate member is in the first configuration when the insert is in the first configuration (e.g., actuator 1132 is in the first position) and the elongate member is in the second configuration when the insert is in the second configuration (e.g., actuator 1132 is in the second position). The balloon is disposed on the elongate member and has a balloon wall that defines a balloon chamber in communication with the inflation lumen. The balloon is moveable between a first deflated configuration and a second inflated configuration as fluid is moved into and out of the balloon chamber. Another step 1206 comprises inserting the cannula into a bodily passage such that the cannula distal end is disposed within the bodily passage. Another step 1208 comprises navigating the cannula toward a point of treatment within the bodily passage. The point of treatment comprises an opening defined by the wall of the bodily passage. Another step 1210 comprises advancing the elongate member distally through the cannula lumen such that the portion of the insert that defines the insert curve is free of, or disposed outside of, the cannula lumen. Another step 1212 comprises moving the actuator of the insert from the first position to the second position such that the insert moves to the second curved configuration and the elongate member moves to the second curved configuration. Another step 1214 comprises navigating the elongate member distal end toward the opening defined by the passage wall. Another step 1216 comprises advancing the elongate member distal end through the opening defined by the passage wall such that the balloon is positioned through the opening. Another step 1218 comprises passing a fluid through the inflation lumen and into the balloon chamber to move the balloon toward the second inflated configuration.

Another step 1220 comprises stopping the step of passing a fluid through the inflation lumen and into the balloon chamber. Another step 1222 comprises removing a portion of the fluid from the balloon chamber. Another step 1224 comprises withdrawing the elongate member from the opening defined by the passage wall. Another step 1226 comprises moving the actuator of the insert from the second position to the first position such that the insert moves to the first configuration and the elongate member moves to the first curved configuration. Another step 1228 comprises withdrawing the catheter from the cannula lumen. Another step 1230 comprises withdrawing the cannula from the bodily passage.

Step 1202 can be accomplished by selecting any suitable insert according to an embodiment, such as the embodiments described and illustrated herein. Skilled artisans will be able to second a suitable insert according to a particular embodiment based on various considerations, including the treatment intended to be performed. Examples of inserts considered suitable include, but are not limited to, insert 1100, and any other insert capable of moving between a first straight, or substantially straight, configuration and a second curved configuration.

Step 1204 can be accomplished using any suitable cannula and/or catheter according to an embodiment, such as the embodiments described and illustrated herein. Skilled artisans will be able to select a suitable cannula and/or catheter according to a particular embodiment based on various considerations, including the treatment intended to be performed. Examples of cannulas considered suitable include, but are not limited to, cannula 200, cannula 600, and any other cannula described herein and/or considered suitable for a particular application. Examples of catheters considered suitable include, but are not limited to, catheter 220, catheter 620, and any other catheter described herein and/or considered suitable for a particular application.

Step 1204 can be accomplished by introducing the insert distal end into the proximal opening of a device lumen of a catheter and applying a distally-directed force on the insert until the distal end of the deflectable member of the insert is disposed proximal to the distal end of the catheter, the connector of the insert contacts the proximal end of the elongate member, and/or until the portion of the deflectable member that defines the insert curve is entirety, or partially, disposed within the device lumen of the elongate member.

Alternatively, an insert can be pre-loaded within an elongate member such that steps 1202 and 1204 can be omitted from method 1200. An insert can be pre-loaded and/or inserted into any suitable catheter, such as those described herein. For example, any of the catheters described herein can include a lumen that extends from an opening on the proximal end of the catheter toward the distal end of the catheter (e.g., an opening on the distal end of the catheter) and any of the inserts described herein can be advanced into, or positioned within, the lumen defined by the catheter.

Step 1206 can be accomplished as described above with respect to step 102. Step 1208 can be accomplished as described above with respect to step 106. Step 1210 can be accomplished as described above with respect to step 108.

Step 1212 can be accomplished by applying a proximally-directed force (e.g., toward the proximal end of the elongate member) on the actuator while maintaining the position of the elongate member of the insert such that the actuator moves from the first position to the second position, the deflectable member moves from the first straight, or substantially straight, configuration to the second curved configuration, and the elongate member moves from the first straight, or substantially straight, configuration to the second curved configuration. Alternatively, the position of the actuator can be maintained while a distally-directed force (e.g., toward the distal end of the deflectable member) is applied on the elongate member, or a proximally-directed force can be applied on the actuator while a distally-directed force is applied on the elongate member, to move the actuator to the second position.

Step 1214 can be accomplished as described above with respect to step 110. Step 1216 can be accomplished as described above with respect to step 112. Step 1218 can be accomplished as described above with respect to step 114. Step 1220 can be accomplished as described above with respect to step 116. Step 1222 can be accomplished as described above with respect to step 118. Step 1224 can be accomplished as described above with respect to step 120.

Step 1226 can be accomplished by applying a distally-directed force (e.g., toward the distal end of the elongate member) on the actuator while maintaining the position of the elongate member of the insert such that the actuator moves from the second position to the first position, the deflectable member moves from the second curved configuration to the first straight, or substantially straight, configuration, and the elongate member moves from the second curved configuration to the first straight, or substantially straight, configuration. Alternatively, the position of the actuator can be maintained while a proximally-directed force (e.g., toward the proximal end of the elongate member) is applied on the elongate member, or a distally-directed force can be applied on the actuator while a proximally-directed force is applied on the elongate member, to move the actuator to the first position.

Step 1228 can be accomplished as described above with respect to step 122. Step 1230 can be accomplished as described above with respect to step 124. When an insert is disposed within an elongate member, as described herein, any of the steps described herein that include applying a force to a catheter and/or elongate member can optionally include simultaneously, or separately, applying a force in the same direction as the force applied to the catheter and/or elongate member on an insert.

It is considered advantageous to complete method 1200 in the order illustrated and/or described. It is noted, however, that any order is considered suitable.

While various steps, alternative steps, and optional steps have been described above with respect to treating tissue in a passage wall defining a bodily passage, these steps, alternative steps, and optional steps can be included in, accomplished concurrently with, and/or accomplished in the alternative to, the methods, steps, alternative steps, and/or optional steps described above with respect to treating tissue in a passage wall defining a bodily passage and/or treating tissue in a passage wall defining a sinus passage.

The foregoing detailed description provides exemplary embodiments of the invention and includes the best mode for practicing the invention. The description and illustration of embodiments is intended only to provide examples of the invention, and not to limit the scope of the invention, or its protection, in any manner.

What is claimed is:

1. A delivery device, comprising:
   a housing having a housing proximal end, a housing distal end, and a housing body defining a housing lumen;
   a cannula having a cannula proximal end, a cannula distal end, and a cannula body defining a cannula lumen, the cannula attached to the housing such that the housing lumen and the cannula lumen are in communication;

a pusher having a pusher proximal end, a pusher distal end slidably disposed within the housing lumen, and a pusher body that defines a pusher lumen, the pusher moveable between a pusher first configuration and a pusher second configuration; and a catheter attached to the pusher and having at least a portion disposed within the cannula lumen, the catheter comprising an elongate member and a balloon, the elongate member having an elongate member proximal end, an elongate member distal end, and an elongate member body defining an inflation lumen in communication with the pusher lumen and an elongate member curve, the balloon disposed on the elongate member and having a wall defining a balloon chamber in communication with the inflation lumen, the balloon moveable between a first deflated configuration and a second inflated configuration as fluid is moved into and out of the balloon chamber, the elongate member adapted to move between a first substantially straight configuration in which the portion of the elongate member that defines the elongate member curve is substantially straight when disposed within the cannula lumen and a second curved configuration when the portion of the elongate member that defines the elongate member curve is free of the cannula lumen.

2. The delivery device of claim 1, wherein the elongate member has an elongate member first axis and an elongate member second axis, the elongate member first axis extending along a portion of the elongate member body disposed proximal to the elongate member curve, the elongate member second axis extending through the elongate member first axis and the elongate member distal end; and wherein the elongate member second axis is disposed at an angle to the elongate member first axis.

3. The delivery device of claim 2, wherein the elongate member second axis is disposed at an angle selected from the group consisting of a substantially 45 degree angle, a substantially 90 degree angle, and a substantially 135 degree angle to the elongate member first axis.

4. The delivery device of claim 2, wherein the elongate member second axis is disposed at a substantially 90 degree angle to the elongate member first axis.

5. The delivery device of claim 2, wherein the elongate member curve is defined between the elongate member proximal end and the elongate member distal end.

6. The delivery device of claim 2, wherein the elongate member curve is defined from a location between the elongate member proximal end and the elongate member distal end to the elongate member distal end.

7. The delivery device of claim 6, wherein the elongate member second axis is disposed at an angle selected from the group consisting of a substantially 45 degree angle, a substantially 90 degree angle, and a substantially 135 degree angle to the elongate member first axis.

8. The delivery device of claim 6, wherein the elongate member second axis is disposed at a substantially 90 degree angle to the elongate member first axis.

9. The delivery device of claim 2, wherein the elongate member curve is defined between the balloon and the elongate member distal end.

10. The delivery device of claim 9, wherein the elongate member second axis is disposed at an angle selected from the group consisting of a substantially 45 degree angle, a substantially 90 degree angle, and a substantially 135 degree angle to the elongate member first axis.

11. The delivery device of claim 10, wherein the elongate member second axis is disposed at a substantially 90 degree angle to the elongate member first axis.

12. The delivery device of claim 9, wherein the elongate member second axis is disposed at a substantially 90 degree angle to the elongate member first axis.

13. The delivery device of claim 2, wherein the balloon has a balloon proximal end and a balloon distal end; and wherein the elongate member curve is defined between the balloon distal end and the elongate member distal end.

14. The delivery device of claim 13, wherein the elongate member second axis is disposed at an angle selected from the group consisting of a substantially 45 degree angle, a substantially 90 degree angle, and a substantially 135 degree angle to the elongate member first axis.

15. The delivery device of claim 2, wherein a portion of the elongate member contacts the cannula body when the elongate member is in the first substantially straight configuration.

16. A delivery device, comprising:

a housing having a housing proximal end, a housing distal end, and a housing body defining a housing lumen;

a cannula having a cannula proximal end, a cannula distal end, and a cannula body defining a cannula lumen, the cannula attached to the housing such that the housing lumen and the cannula lumen are in communication;

a pusher having a pusher proximal end, a pusher distal end slidably disposed within the housing lumen, and a pusher body that defines a pusher lumen, the pusher moveable between a pusher first configuration and a pusher second configuration; and a catheter attached to the pusher and having at least a portion disposed within the cannula lumen, the catheter comprising an elongate member and a balloon, the elongate member having an elongate member proximal end, an elongate member distal end, and an elongate member body defining an inflation lumen in communication with the pusher lumen and an elongate member curve, the balloon disposed on the elongate member and having a wall defining a balloon chamber in communication with the inflation lumen, the balloon moveable between a first deflated configuration and a second inflated configuration as fluid is moved into and out of the balloon chamber, the elongate member adapted to move between a first substantially straight configuration in which the portion of the elongate member that defines the elongate member curve is substantially straight and a second curved configuration;

wherein the elongate member curve is defined between the balloon and the elongate member distal end; and wherein the elongate member is biased to the second curved configuration.

17. The delivery device of claim 16, wherein the elongate member curve is defined between the balloon distal end and the elongate member distal end.

18. The delivery device of claim 16, wherein the elongate member has an elongate member first axis and an elongate member second axis, the elongate member first axis extending along a portion of the elongate member body disposed proximal to the elongate member curve, the elongate member second axis extending through the elongate member first axis and the elongate member distal end; and wherein the elongate member second axis is disposed at an angle to the elongate member first axis.

19. The delivery device of claim 16, wherein the elongate member second axis is disposed at a substantially 90 degree angle to the elongate member first axis.

20. A delivery device, comprising:
- a housing having a housing proximal end, a housing distal end, and a housing body defining a housing lumen;
- a cannula having a cannula proximal end, a cannula distal end, and a cannula body defining a cannula lumen, the cannula attached to the housing such that the housing lumen and the cannula lumen are in communication;
- a pusher having a pusher proximal end, a pusher distal end slidably disposed within the housing lumen, and a pusher body that defines a pusher lumen, the pusher moveable between a pusher first configuration and a pusher second configuration; and
- a catheter attached to the pusher and having at least a portion disposed within the cannula lumen, the catheter comprising an elongate member and a balloon, the elongate member having an elongate member proximal end, an elongate member distal end, and an elongate member body defining an inflation lumen in communication with the pusher lumen and an elongate member curve, the balloon disposed on the elongate member and having a wall defining a balloon chamber in communication with the inflation lumen, the balloon moveable between a first deflated configuration and a second inflated configuration as fluid is moved into and out of the balloon chamber, the elongate member adapted to move between a first substantially straight configuration in which the portion of the elongate member that defines the elongate member curve is substantially straight and a second curved configuration;
- wherein the elongate member curve is defined between the balloon distal end and the elongate member distal end;
- wherein the elongate member is biased to the second curved configuration;
- wherein the elongate member has an elongate member first axis and an elongate member second axis, the elongate member first axis extending along a portion of the elongate member body disposed proximal to the elongate member curve, the elongate member second axis extending through the elongate member first axis and the elongate member distal end; and
- wherein the elongate member second axis is disposed at a substantially 90 degree angle to the elongate member first axis.

* * * * *